(12) United States Patent
Juhasz

(10) Patent No.: US 6,619,112 B2
(45) Date of Patent: Sep. 16, 2003

(54) APPARATUS FOR TESTING THE ABILITY OF A FILTER TO FILTER CONTAMINANTS

(76) Inventor: Charles Juhasz, P.O. Box 1464, Apex, NC (US) 27502

( * ) Notice: Subject to any disclaimer, the term of this patent is extended or adjusted under 35 U.S.C. 154(b) by 0 days.

(21) Appl. No.: 10/183,769

(22) Filed: Jun. 25, 2002

(65) Prior Publication Data

US 2003/0078751 A1 Apr. 24, 2003

Related U.S. Application Data

(62) Division of application No. 09/216,434, filed on Dec. 18, 1998, now Pat. No. 6,453,257.

(51) Int. Cl.[7] .................. B01D 35/1143; G01M 19/00
(52) U.S. Cl. .................. 73/168; 73/37; 73/865.9
(58) Field of Search .................. 73/168, 38, 37, 73/865.9, 61.41, 61.47, 61.63, 61.64, 61.78; 702/114

(56) References Cited

U.S. PATENT DOCUMENTS

| | | | | | |
|---|---|---|---|---|---|
| 3,478,601 A | * | 11/1969 | Niebergall | .................. | 73/38 X |
| 3,505,876 A | * | 4/1970 | Niebergall | .................. | 73/865.9 |
| 3,824,823 A | | 7/1974 | Dontello | | |
| 4,044,604 A | | 8/1977 | Russ | | |
| 4,188,970 A | | 2/1980 | Maidment et al. | | |
| 4,311,436 A | * | 1/1982 | Hendriks | .................. | 73/168 X |
| 4,449,392 A | * | 5/1984 | Huschke | .................. | 73/38 X |
| 4,513,606 A | * | 4/1985 | Rhynard | .................. | 73/61.41 |
| 5,563,334 A | | 10/1996 | Bracht et al. | | |
| 2002/0162778 A1 | * | 11/2002 | Peabody et al. | .................. | 210/85 |
| 2003/0033106 A1 | * | 2/2003 | Von Der Hardt et al. | ... | 702/114 |

FOREIGN PATENT DOCUMENTS

| | | |
|---|---|---|
| DE | 3917856 A1 | 12/1989 |
| JP | 58-208640 | 12/1983 |
| JP | 62-169211 | 7/1987 |
| JP | 4-93747 * | 3/1992 .................. 73/168 |

OTHER PUBLICATIONS

Derwent–Acc–No. 1977–015104 abstract of SU–512408 A Zaslavskii "Liquid Fuels Filters effectiveness tester—contains fuel circulating pump, contaminants injection flow meter and differential manometer".

Derwent–Acc–No. 1984–004828—abstract of SU 1000597 A Chumachenk et al. Contaminated liquid pump test stand—has water jet connected to bypass line through valve fed by program control unit.

Derwent–Acc–No. 1987—312706 abstract of SU 1291850 A Galkin et al. Test device of porous filter properties has hydro—cyclone to pass increased pressure through valve to contaminant dispenser and uses circulating flow to mix contaminant uniformly with test liquid.

* cited by examiner

*Primary Examiner*—Thomas P. Noland
(74) *Attorney, Agent, or Firm*—Daniel J. O'Neill

(57) ABSTRACT

The present invention is directed towards an apparatus for testing hydraulic components. The apparatus includes a test fixture for housing a hydraulic component to be tested, a first fluid reservoir containing fluid substantially free of contaminants, contaminant monitoring and pressure monitoring systems for monitoring the respective contaminants at, and the pressure drop across, the inlet and the outlet of the test fixture. The apparatus includes a plurality of second fluid reservoirs. Each second fluid reservoir can contain a slurry consisting of a known volume of fluid mixed with a charge of contaminants of known mass and can discharge this contaminant slurry into the inlet of the test fixture. Each second reservoir can be filled with fluid from the first fluid reservoir. One second reservoir can discharge its contaminant slurry into the inlet of the test fixture while one or more other second reservoirs receives fluid from the first reservoir.

3 Claims, 24 Drawing Sheets

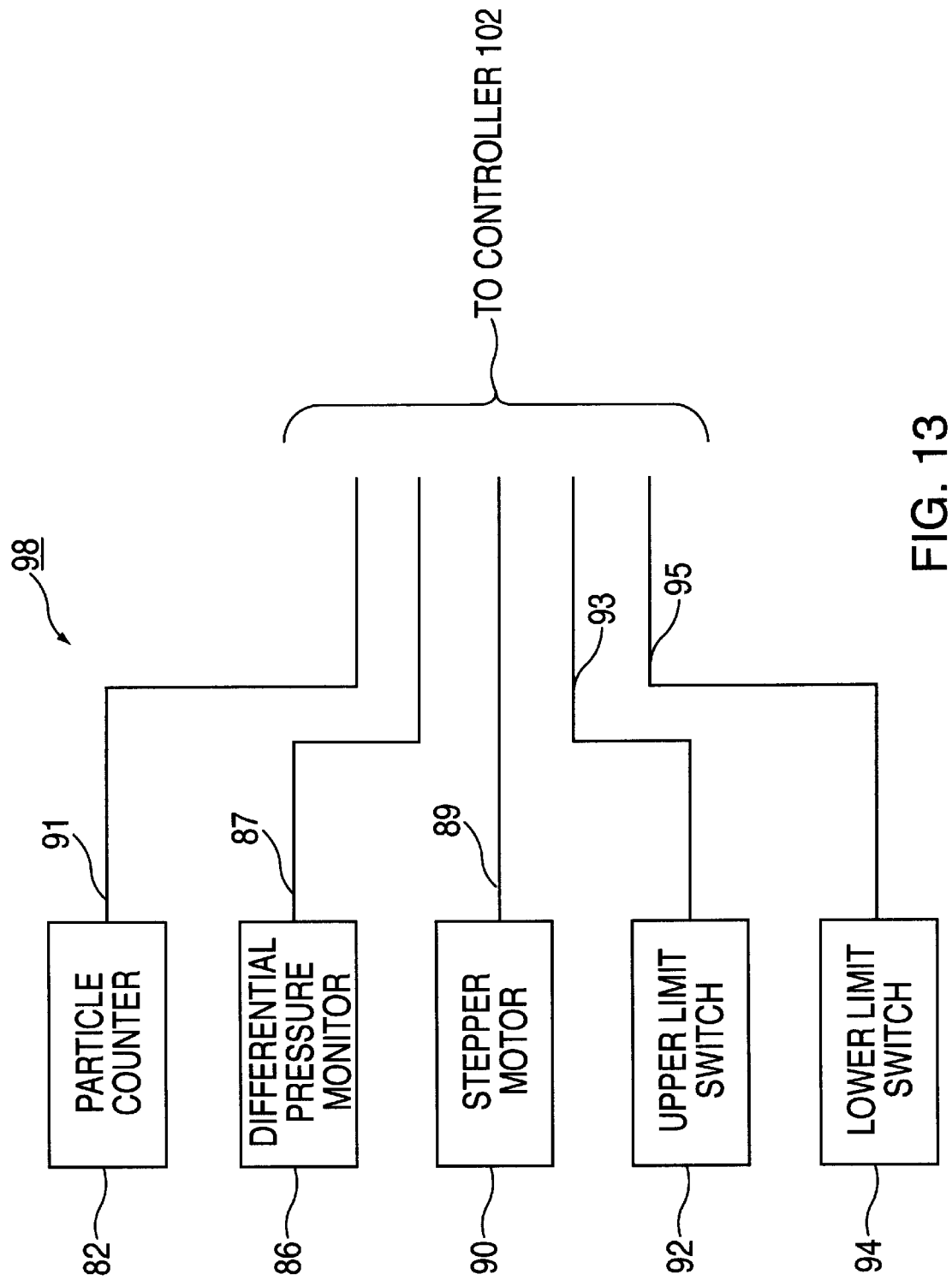

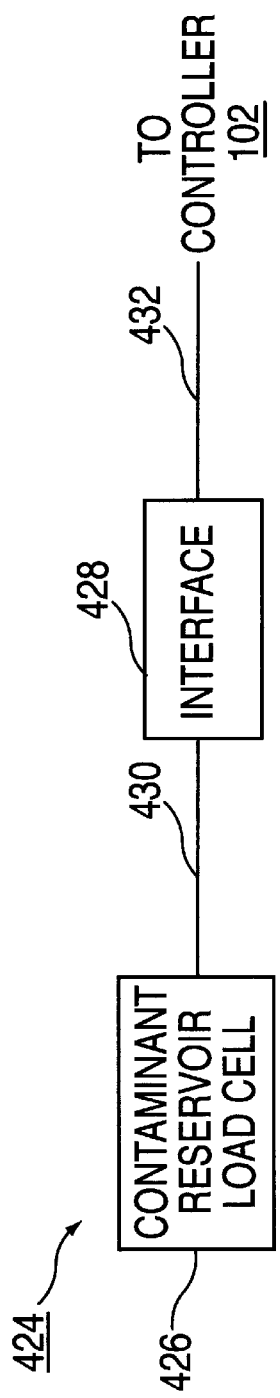
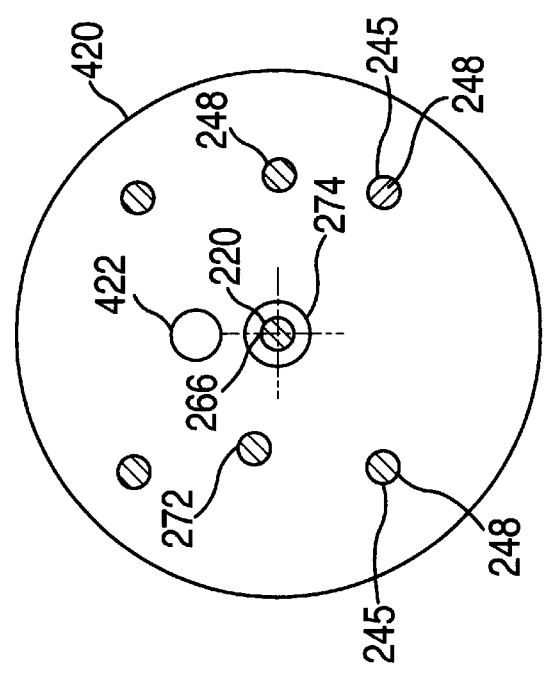
FIG. 26
FIG. 25

TEST REPORT FORMAT

TABLE OF CONTENTS
DESCRIPTION OF TEST 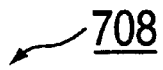
TEST SPECIFICATIONS
FLOW/PRESSURE DROP DATA:
    FIXTURE, FIXTURE/FILTER, FILTER
FLOW PRESSURE DROP PLOT
SYSTEM (BACK GROUND) CLEANLINESS DATA
FILTER INITIAL CLEANLINESS DATA
FILTER FINAL CLEANLINESS DATA
DYNAMIC EFFICIENCY FILTRATION TEST DATA
FILTRATION EFFICIENCY/PRESSURE DIFFERENTIAL PLOT
    IN A MINIMUM OF 6 PARTICLE SIZES
    (E.G. 3, 5, 10, 15, 25 AND 50 MICROMETER)
CONTAMINANT CAPACITY/FILTER LIFE PLOT
NUMERICAL SUMMARY, INCLUDING TIME AVERAGE
    TOTAL PERFORMANCE DATA
INTERPRETATION OF RESULTS
REFERENCES

FIG. 37

APPARATUS FOR TESTING THE ABILITY OF A FILTER TO FILTER CONTAMINANTS

This is a division of application Ser. No. 09/216,434, filed Dec. 18, 1998, now U.S. Pat. No. 6,453,257.

BACKGROUND OF THE INVENTION

The present invention relates to an apparatus for testing the ability of a filter to filter contaminants, and more particularly to an apparatus for automatically testing the ability of filters to filter solid contaminants from a fluid.

Many machines circulate oil for lubricating moving parts or use hydraulic fluid to transmit power or control signals. All of these machines use filters to remove contaminants from the fluid circulated in order to maintain their performance, reliability and desired longevity. The filters maintain the size and count of solid contaminant particles below specified limits. In order to determine if a filter can function as intended it is necessary to define and evaluate its performance. The performance of filters is tested both to predict the performance of the filter in its actual operation and to compare the performance of filters of different design, construction and characteristics.

The ability of a filter to remove contaminants is the subject of various standards, such as ISO 16889. While the test systems called for in these specifications generally perform adequately, there is a need for a more accurate, more automated, more flexible and user friendly test system. Such a test system should be able to conduct tests of both single pass filtration efficiency and multi-pass filtration efficiency. Single pass filtration efficiency is the particle removal efficiency of a filter in applications where the fluid passes the filter only once and is not returned for repeated passes through the filter (e.g., fuel filters and reservoir filling filters). Multipass filtration efficiency is the particle removal efficiency of a filter in applications in which the same fluid continuously recirculates through the filter (e.g., hydraulic or lubricating systems). A comprehensive filter test should be able to evaluate filter performance based on some or all of the following parameters:

Particulate Removal Efficiency (i.e., the effectiveness of the filter expressed as the percentage of the number of particles in specific size ranges removed from the flow of fluid passing through the filter) based on the Filtration Ratio (i.e., the number of particles in a specific size range entering the filter, divided by the number of particles in the same size range exiting the filter);

Filter Life based on the Apparent Contaminant Capacity (i.e., the quantity of contaminant injected into a filter causing the differential pressure across the filter to rise to a specific value);

Pressure Loss based on the Flow/Differential pressure relationship; and

Structural Integrity based on the maximum differential pressure the filter is capable of withstanding without loss of filtration efficiency.

SUMMARY OF THE INVENTION

The present invention is embodied in a test system for automatically testing a fluid filter or other hydraulic component or system according to one or more test parameters. The test system is positioned at a first location and includes a test fluid path having substantially a closed loop path through the hydraulic component under test and a controller, capable of receiving one or more operational parameters associated with the hydraulic component test system, that monitors one or more of the operational parameters, controls the operation of the test system and calculates and reports the results of a test conducted by the hydraulic component test system. The controller includes memory that stores data related to the operational parameters monitored by the controller during the course of a test and capable of storing a test program, and a test program, stored in the memory, that includes one or more test parameters specifying how the test is to be conducted, for operating the controller in the course of the test. The test system also includes the following: a local input device operably connected to the controller and configured to convey to the test program one or more test parameters; a test fixture that houses the hydraulic component to be tested, the test fixture including inlet and outlet connections in fluid communication with the test fluid path; a main fluid reservoir system, operably connected to and controlled by the controller and capable of containing a supply of fluid that is substantially free of contaminants before a test is commenced, and including a main fluid reservoir tank having a fluid inlet and a fluid outlet, the inlet and outlet each in fluid communication with the test fluid path; a contaminant injection system capable of containing a supply of contaminated fluid, that includes at least one contaminant tank, each tank capable of containing a supply of contaminated fluid and having a fluid outlet in fluid communication with the test fluid path upstream of the test fixture, for introducing contaminants into the fluid flowing into the test component, and a contaminant fluid flow control device, operably connected to and controlled by the controller and in fluid communication with and positioned between each contaminant tank outlet and the test fluid path, that controls the flow of fluid from each contaminant tank into the test fluid path upstream of the test mixture; a contaminant monitoring system that includes an upstream contaminant monitor, operably connected to and controlled by the controller and in fluid communication with the test fluid path at a position near the inlet of the test fixture, that monitors the contaminant level of fluid in the test fluid path upstream of the test fixture and reports the monitored contaminant level of the controller, and a downstream contaminant monitor, operably connected to and controlled by the controller and in fluid communication with the test fluid path at a position near the outlet of the test fixture, that monitors the contaminant level of fluid in the test fluid path downstream of the test fixture and reports the monitored contaminant level to the controller; a component fluid pressure monitoring system, operably connected to the controller and in fluid communication with the test fluid path near the inlet of the test fixture and near the outlet of the test fixture, that monitors the pressure change across the test fixture and reports the monitored pressure change to the controller; a pumping system, operably connected to and controlled by the controller and in fluid communication with the test fluid path, that controllably drives fluid through the test fluid path; and a system fluid flow rate measuring device, operably connected to the controller and in fluid communication with the test fluid path in substantial proximity to the test fixture, that measures the fluid flow rate through the test fixture and reports the measured fluid flow rate to the controller. The test program operates the controller to conduct a test of the test component, including controlling the operation of the hydraulic component test system in response to one or more test parameters and one or more operational parameters reported to the controller.

The operational parameters reported to the controller and used by the test program to conduct the test of hydraulic component may include the pressure change across the test fixture, the fluid flow rate through the test fixture, and the contaminant levels measured by the upstream and downstream contaminant monitors.

The test system may include a local monitor device, operably connected to the controller, that receives from the controller and displays at least one operational parameter reported to the controller and the test results reporting by the controller.

The test system may include a second location separate from the first location. The two locations are linked by a communication system, such as a telephone or the Internet. At the second location is a remote monitor device that connects to the controller via the communication system. The remote monitor device receives from the controller and displays at least one operational parameter reported to the controller. Also located at the second location is a remote input device. The remote input device connects to the controller via the communication system and conveys to the test program one or more test program parameters.

The main fluid reservoir system may include a main fluid reservoir tank support structure, connected to the main fluid reservoir tank and positioned at the first location, that supports the main fluid reservoir tank at the location. This structure may further include a first scale operably connected to the controller and positioned with respect to the first reservoir tank to measure the mass of fluid in the first reservoir tank.

The controller test program may further include a program that controls an external fluid supply flow control device to fill the main fluid reservoir tank with a predetermined amount of fluid prior to the controller conducting the test of hydraulic component. This program includes a program that orders the external fluid supply flow control device to stop the flow of fluid from an external fluid supply into the main fluid reservoir tank in response to a reported mass measurement from the first scale that indicates the amount of fluid in the in the main fluid reservoir tank has reached a predetermined amount of fluid.

The hydraulic component test system may include devices that monitor the rate of fluid flow through its contaminant monitors and a program in its controller that calculates the concentration of contaminants going into and coming out of the hydraulic component under test based on the counts of particles of contaminants in the fluid passing through contaminant monitors and the measured fluid flow rate through the monitors while also maintaining the flow of fluid through the contaminant monitors within a desired range.

To control the flow of fluid past the contaminant monitors, the hydraulic component test system may include upstream and downstream measuring fluid path flow control and flow rate measuring devices. Each of these devices include: a first capillary in fluid communication with the respective upstream and downstream measuring fluid paths and having an inlet and an outlet; a first capillary pressure monitor, operably connected to the controller and in fluid communication with the inlet and outlet of the first capillary, that measures the pressure change across the first capillary and reports the measurement to the controller; and a first controllable valve, in fluid communication with the first capillary and operably connected to and controlled by the controller, that controls the fluid flow through the first capillary. The controller test program includes a program that controls the fluid flow through the first capillaries of the upstream and downstream measuring fluid path flow control and flow rate measuring devices in response to the respective pressures reported by the associated first capillary pressure monitors. The controllable valves can be needle valves operated by stepping motors.

The pumping system the of hydraulic component test system may include a test pump that pumps fluid through the test fluid path, a hydraulic motor that drives the pump, and a hydraulic pump that connects to the hydraulic motor via hydraulic fluid lines that provides the fluid flow volume in the first hydraulic lines to drive the hydraulic motor. The hydraulic motor may be driven by a variable displacement pump having a rotor and operably connected to and controlled by the controller such that the controller can control the pitch of the rotor, thereby controlling the volume of fluid transmitted by the hydraulic pump to the hydraulic motor via the hydraulic lines and in turn controlling the rotational speed of the hydraulic motor.

In the hydraulic component test system, the contaminant injection system may include a contaminated fluid flow rate measuring device that measures the flow rate of contaminated fluid from the contaminant injection system into the test fluid path and reports the measurements to the controller. The controller test program includes a program that causes the controller to control the contaminant fluid flow control device to control the flow of contaminated fluid into the test fluid path in response to the contaminated fluid flow rate measured and reported to the controller by the contaminated fluid flow rate measuring device. The flow rate may be determined by using an integral scale to measure the mass of fluid in the contaminant tanks with respect to time, and calculating the flow rate based on the known density of the fluid. Alternatively, the flow rate may be determined using a device similar to the device that may be used to measure the fluid flow rate through the contaminant monitoring system.

The contaminant injection system may include a metering pump that the controller controls to vary the fluid flow rate from the contaminant injection system based on the measure fluid flow rate.

The contaminant injection system may include multiple contaminant injection tanks, with one tank being used to supply the test system with contaminated fluid while one or more of the other tanks are being automatically refilled with fluid and with contaminants in a predetermined amount.

BRIEF DESCRIPTION OF THE DRAWINGS

FIG. 13 is a block diagram of the connections between the controller of FIG. 2 and certain components of the contamination monitor of FIG. 12.

FIG. 25 is a top view of a top plate of the reservoir 15 of FIG. 23 showing the opening for adding a precise charge of contaminants.

FIG. 26 is a block diagram of the scale of the contaminant injection subsystem of FIG. 23.

FIG. 37 is a summary of the contents of a test report for report step of FIG. 32.

DESCRIPTION OF THE PREFERRED EMBODIMENTS

Overview of System Architecture

This disclosure incorporates by reference application Ser. No. 09/216,434, filed Dec. 18, 1998, now U.S. Pat. No. 6,453,257.

Figure 1:
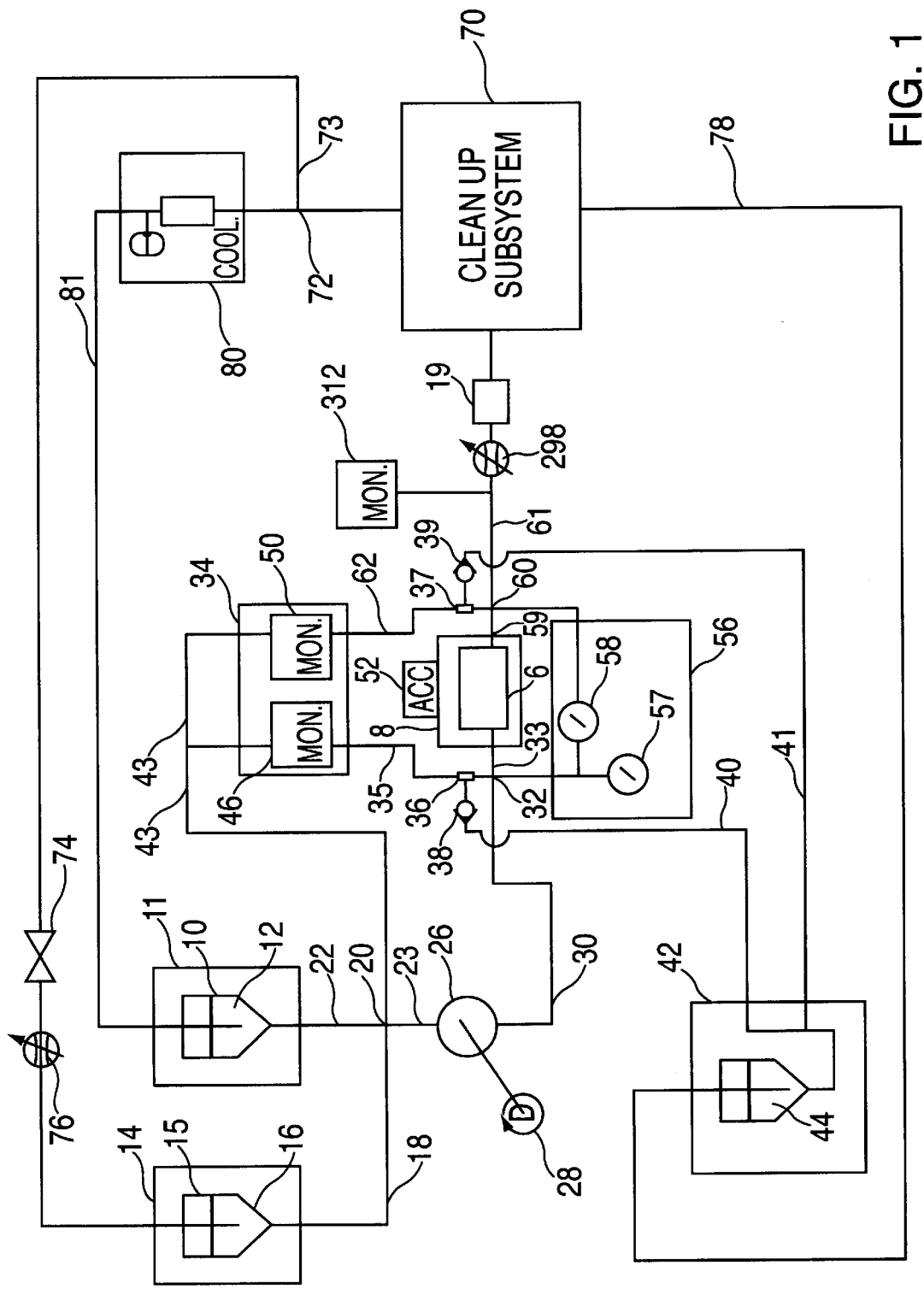
FIG. 1 is a high level block diagram of the fluid filter test system of the present invention, showing the main subsystems of the test system and the fluid connections between them.
Figure 2:
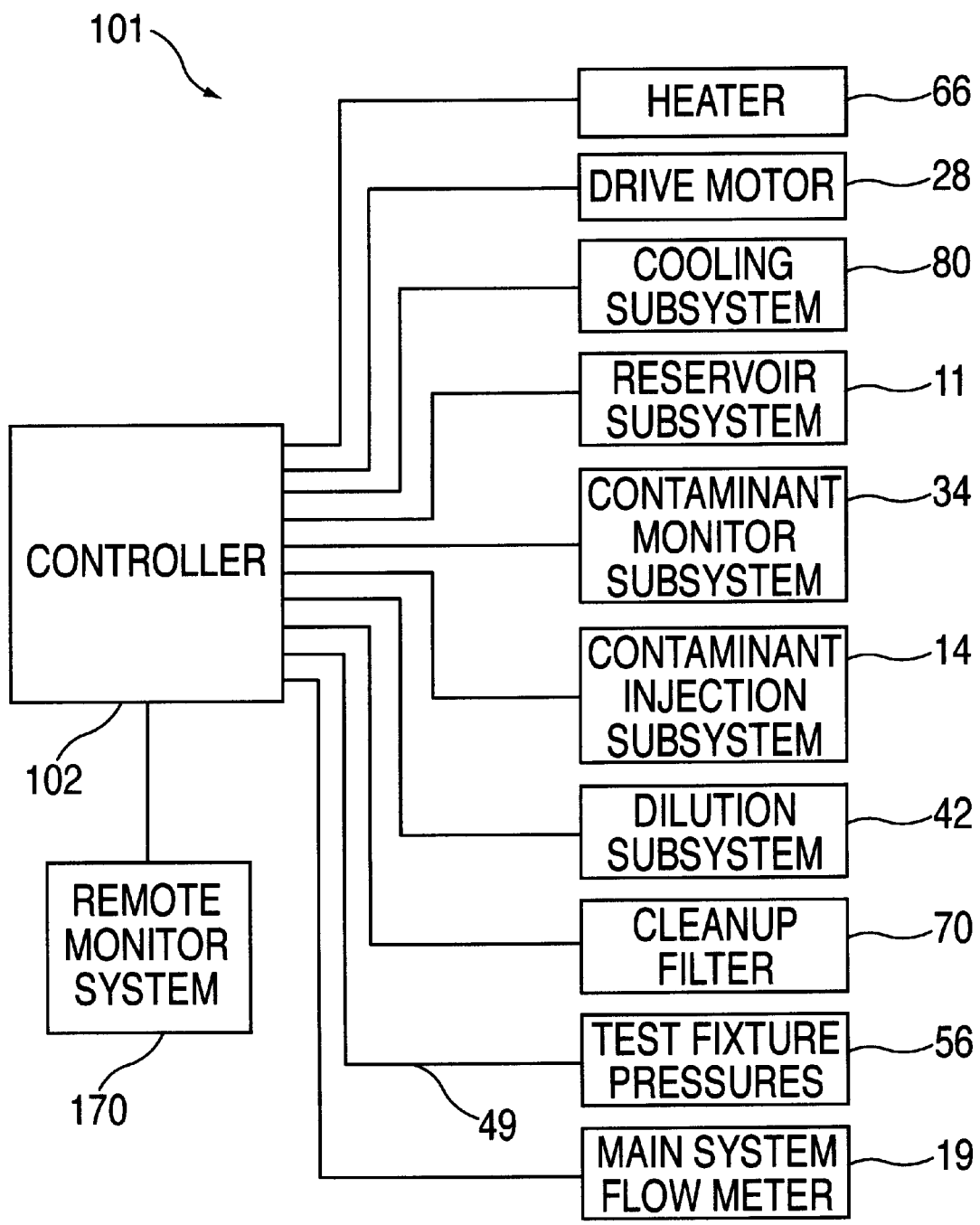
FIG. 2 is a high level block diagram of the control system for the fluid filter test system of FIG. 1.

Referring now to FIGS. 1 and 2, FIG. 1 depicts a high level block diagram of the fluid system architecture of test system 100 of the present invention. Shown in FIG. 1 are the main components and subsystems of test system 100. FIG. 2 depicts a high level block diagram of the control system architecture 101 of the fluid test system 100 of FIG. 1. Shown in FIG. 2 are blocks representing the main components and subsystems, controller 102 which is connected to and controls these components and subsystems and remote monitor system 170 which connects to controller 102 to monitor and/or control test system 100 from a remote site. Test system 100 is suitable for manual operation by an operator (not shown), but preferably conducts tests automatically under control of controller 102 to facilitate the accuracy and repeatability of test results. Preferably test system 100 can be configured under control of controller 102 for both single pass tests (i.e., in which fluid is circulated once through test filter 6) and multipass tests (i.e., in which fluid is recirculated through test filter 6), such as ISO 4572.

Existing filter tests (such as ISO 4572) are generally adequate. However, they fall short of adequately describing filter performance because they rate filter performance on limited number of data points or numbers (e.g., five) under steady state conditions within the performance envelope of the filter. A more useful test is the Dynamic Efficiency Test Method developed by the inventor of the present invention and described in greater detail in the section below entitled, "Operation of Test System."

This overview section briefly describes the main components and subsystems of test system 100 and their interrelation. Detailed descriptions of the features of these individual components and subsystems and of the operation of test system 100 are provided below in the appropriately titled sections.

Referring now to FIGS. 1 and 2, controller 102 is operably connected to and controls the other components and subsystems of test system 100. Fluid reservoir subsystem 11 includes reservoir 10 that supplies certain components of test system 100 with relatively contaminant free or "clean" fluid 12. Contaminant injection subsystem 14 includes one or more reservoirs 15 that supply contaminated fluid 16 to mix with relatively clean fluid 12. Such mixed fluid is pumped by test pump 26 through test fixture 8 that holds a filter 6 under test. The flow rate of fluid through test filter 6 is measured by test flow meter 19 positioned downstream of test fixture 8.

Contamination monitoring subsystem 34 includes upstream monitor 46 and downstream monitor 50 that monitor the concentration of different size contaminant particles in fluid diverted from the inlet and outlet of test fixture 8, respectively. Typically monitors 46 and 50 cannot accurately measure the concentration of contaminants in the diverted fluid if that concentration exceeds a certain threshold. To allow monitors 46 and 50 to accurately measure contamination when the concentration exceeds this threshold, under control of controller 102, each monitor 46 and 50 can dilute the fluid it monitors with a precise amount of substantially contaminant free fluid 44 from dilution subsystem 42. Controller 102 adjusts the contamination measurements received from monitors 46 and 50 to reflect the amount of dilution provided by dilution subsystem 42. Note that fluid 44 preferably contains a lesser degree of contaminants than the substantially clean fluid 12 that fills reservoir 12, since any contaminants in fluid 44 can skew the contamination measurements of monitors 46 and 50.

Preferably test system 100 recirculates the fluid flow diverted at junctions 32 and 60 towards contaminant monitoring subsystem 34 to retain the contaminants passing through filter 6 or circulating in test system 100. To this end, pipe 43 connects the outlets of monitors 46 and 50 to junction 20 at the inlet of pump 26.

Cleanup subsystem 70 filters substantially all of the contaminants from the fluid supplied to it. Cleanup subsystem 70 returns most of the fluid processed by it to reservoir subsystem 11: The fluid flows from cleanup subsystem 70 through pipe 71 to cooling subsystem 80 and then through pipe 81 to reservoir subsystem 11. Positioned in pipe 71 is junction 72, which diverts a relatively small portion of the fluid from clean up subsystem 70 through pipe 73 to contaminant injection subsystem 14 to replace fluid 16 injected upstream of test fixture 8. To control the flow of such fluid to subsystem 14, positioned in pipe 73 is shutoff valve 74 and variable valve 76. Clean up subsystem 70 can also provide a relatively small portion of such clean fluid 44 to dilution subsystem 42 via pipe 78 to replace the fluid 44 injected by dilution subsystem 42 into monitoring subsystem 34.

Figure 10:
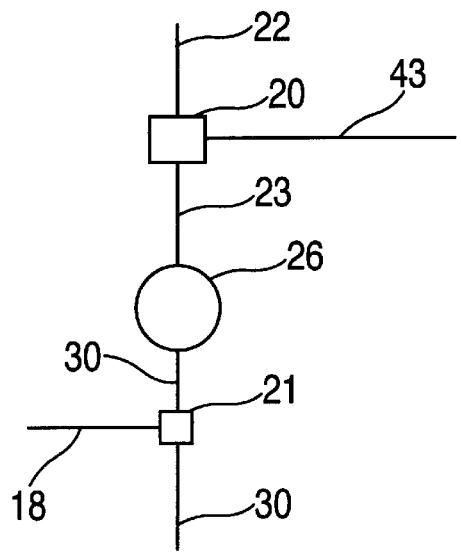
FIG. 10 is a schematic diagram of an alternate configuration for contaminant injection for the test system of FIG. 1.

In operation, contaminants can be injected upstream of test filter 6 either at the inlet of test pump 26 (as shown in FIG. 1) or at the outlet of test pump 26 (as shown in FIG. 10). The choice between injecting contaminated fluid 16 at the inlet or outlet of pump 26 involves design tradeoffs. Where ever fluid 16 is injected, it must be injected in a precise volume. Injecting fluid 16 at the inlet of pump 26 allows for a lower pressure injection of fluid 16, which is less expensive but which subjects pump 26 (an expensive pump) to a greater concentration of contaminants and thus to accelerated wear. Preferably contaminants are injected at the outlet of test pump 26 to save wear on pump 26.

Referring now to FIG. 1, there is shown the configuration by which contaminants are injected at the inlet of pump 26. In particular, contaminated fluid 16 from contaminant subsystem 14 and fluid 12 from reservoir 10 are conveyed by respective pipes 18 and 22 to junction 20, where they mix. Junction 20 also receives fluid from contamination monitor subsystem 34 via pipe 43. Junction 20 is positioned at the inlet side of pump 26, connected to pump 26 by path 23, connected to contaminant injection subsystem 14 by pipe 18 and connected to reservoir subsystem by pipe 22. From the outlet of pump 26, fluid flows through pipe 30 to junction 32.

In FIG. 10 there is shown the configuration by which contaminants are injected at the outlet of pump 26. In particular, pipe 30 conveys fluid from the outlet side of test pump 26 to junction 21, where it mixes with contaminated fluid 16 conveyed from contaminant subsystem 14 by pipe 18. From junction 21, pipe 30 conveys fluid to junction 32 at the inlet of test fixture 8. Note that pump 26 is supplied fluid at its inlet by pipe 23. Pipe 23 also connects to junction 20, to which pipe 22 conveys fluid from reservoir 12 and pipe 43 conveys fluid from contamination monitor subsystem 34.

Referring now to FIGS. 1 and 2, in both embodiments of the present invention, from junction 32 most of the fluid flows through pipe 33 to the inlet of test fixture 8, but a relatively small portion of the fluid flows through pipe 35 to upstream monitor 46.

Fluid entering test fixture 8 is filtered by test filter 6 and then exits test fixture 8 and flows through pipe 59 to junction 60. From junction 60 most of the fluid flows through pipe 61 to cleanup subsystem 70. A relatively small portion of the fluid flows through pipe 62 to the inlet of downstream monitor 50.

Preferably upstream and downstream monitors 46 and 50 can each monitor a relatively large range of contaminant concentration levels of particles of a relatively large range of sizes. Most contamination monitors, however, have an upper limit to the contaminant concentration level they can accurately measure. This upper limit of monitors 46 and 50 can be extended by diluting the fluid flowing into them with a known quantity of relatively clean fluid, with this quantity of clean fluid calculated to bring the contaminant concentration of the now-diluted fluid below the upper threshold of monitors 46 and 50. To this end, under control of controller 102 relatively clean fluid 44 from dilution subsystem 42 flows to monitors 46 and 50 through respective pipes 40 and 41, which attach to respective pipes 35 and 62 at respective mixing chambers 36 and 37 positioned in pipes 35 and 62. Pipes 40 and 41 include respective check valves 38 and 39 to block the flow of fluid in the direction from respective mixing chambers 36 and 37 back to dilution subsystem 42.

Unless otherwise specified for a particular filter test, fluid 12 in test system 100 should hydraulic oil conforming to U.S. Military Standard MIL H 5606 (to standardize performance test data) at a temperature of 36 to 38 degrees Centigrade with conductivity of greater than 1500 pS/M.

The fluid circuits (e.g., pipes and hoses) of test system 100 are constructed of components using practices well known to those skilled in high performance fluid power systems. The maximum possible use is made of preferably is seamless stainless steel. Any hoses have smooth interiors free of contaminants. In design and construction of test system 100 care should be taken to minimize the length of fluid passages and the number of changes in cross sections. Valves and fittings should be of high quality plated steel or stainless steel hydraulic types. Valves and fittings which are cast iron or copper low pressure valves or fittings are unsuitable. Care should be taking to provide adequate grounding to all parts of test system 100 through which fluid circulates, to dissipate the buildup of static charge.

Reservoir Subsystem and Fluid Temperature Monitor

Referring now to FIGS. 1, 2, 3, 7 and 8, reservoir subsystem 11 includes reservoir 10 having sufficient capacity to store the amount of fluid 12 needed to conduct the requisite tests on filter 6. In particular, one frequently employed filter test, ISO 4572, requires reservoir 10 to contain a volume of fluid 12 equal to four times the maximum rated flow of test filter 6.

Reservoir subsystem 11 has a few simple but important tasks to perform. For one, reservoir 10 must be capable of being filled with the precise volume of fluid 12 needed for a particular test. Several methods of measuring the volume of fluid 12 in reservoir 10 are well known to those skilled in the relevant art. One approach is to measure the volume of fluid contained in reservoir 10 can be measured manually, using a calibrated dipstick (not shown). A particularly accurate and cost effective method is for controller 102 to monitor the change in weight of reservoir 10 as reservoir 10 is filled with fluid 12. The mass of fluid 11 in reservoir 10 can be calibrated and displayed by controller 102 as the corresponding volume of fluid 11. As described in greater detail below in this section, reservoir subsystem 11 includes scale 154 connected to and controlled by controller 102 for monitoring the mass of reservoir 10 and associated components and fluid 12.

Another task of reservoir subsystem 11 is to heat fluid 12 to the temperature or range of temperatures required by a particular filter test. Finally, like the other components and subsystems of test system 100, reservoir 10 and components submerged in fluid 12 must be designed and built such that they minimize the contaminants they retain: Proper testing results require all injected contaminants to be either trapped in test filter 6 or in suspension in the fluid circulating through test system 100.

Figure 3:
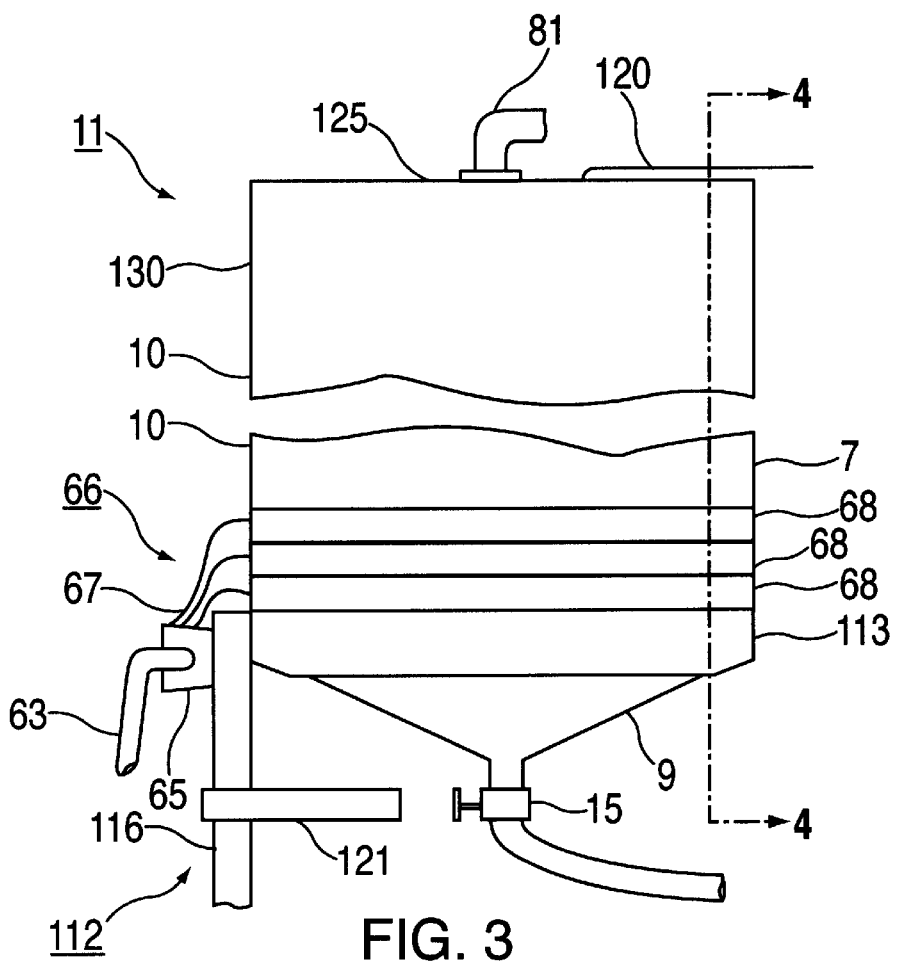
FIG. 3 is a front view of portions of the reservoir of FIG. 1 showing heating elements and partial support structure.

Reservoir subsystem 11 is shown in greater detail in FIG. 3. Reservoir 10 is substantially symmetrical about a vertical axis through its center for simplified construction. Reservoir 10 has an upper portion 7 that is substantially cylindrical in shape and a connecting lower portion 9 that is substantially conical in shape, having its smaller cross-section at its lower end to funnel fluid 12 toward bottom outlet 15 of reservoir 10. Outlet valve 15 is any suitable valve having a smooth interior and an internal opening equal to the inlet and outlet pipe connections. A ball valve or other type of valve with similar characteristics can be used for this purpose. The cylindrical body of upper portion 7 and the conical lower portion 9 minimizes interior horizontal surfaces, thus minimizing the settling of any contaminants present in fluid 12.

To heat fluid 12 to the desired temperatures, reservoir system 11 includes heater 66, connected to and controlled by controller 102, for heating fluid 12 to a temperature determined by controller 102. As shown in FIG. 3, heater 66 includes one or more heating elements 68, power line 67, junction box 65 and cable 63. Preferably heating elements 68 are electric for simplified operation and control, with electric power provided to elements 68 via cable 63, junction box 65 and power line 67.

In the preferred embodiment, each heating element 68 is in the form of a band of resistive heating material, about 0.1 meter wide, that wraps around a horizontal band of the exterior circumference of reservoir 10. The walls of reservoir 10 are constructed of any material or combination of materials of appropriate thickness suitable for conducting heat from heating element 68 to fluid 12. For example, the walls of reservoir 10 could be made of stainless steel or aluminum of a suitable thickness (e.g., 0.095 to 0.125 inches).

Preferably heater 66 includes more than one heating element 68 positioned one above each other around the circumference of reservoir 10. Each element 68 is connected by a separate line 67 to junction box 65. By positioning multiple heating elements 68 in this manner, controller 102 can control the rate at which heat is applied by heater 66 by varying the number of heating elements 68 receiving electric power. Alternatively, controller 102 can vary the electric power received by each heating element 68. This vertical array of heating elements 68 also allows for more efficient heating of fluid 12. Controller 102 can provide power only to those elements positioned vertically near or below the upper surface 69 of fluid 12.

Attaching heating elements 68 to the exterior surface of reservoir 10 is preferred. Less desirable alternatives include attaching heating elements to the inner surface of reservoir 10 (not shown) or positioning coil or rod immersion heaters (not shown) in the interior of reservoir 10 submerged in fluid 12 and either attached to a portion of the interior surface of reservoir 10.

Submersing heating elements in fluid 12 is undesirable because the heating elements can harbor contaminants that, if released into fluid 12, can skew the results of testing.

Figure 4:
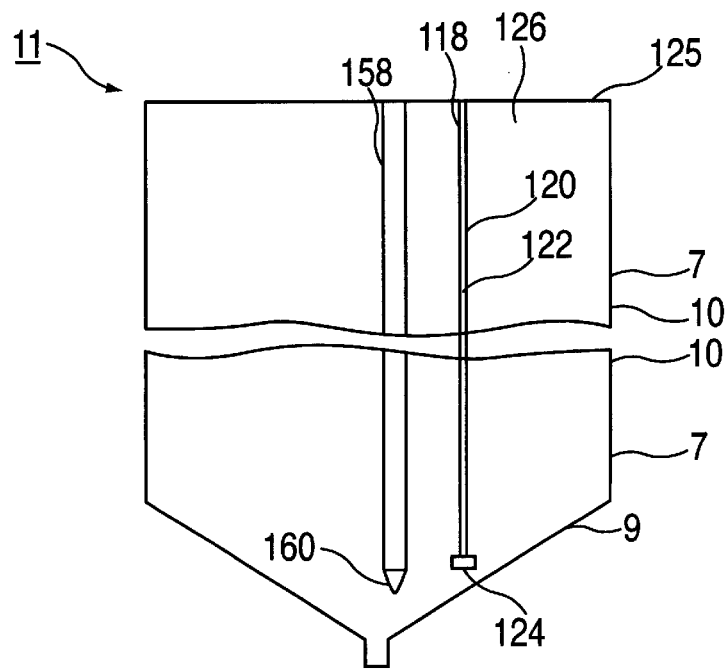
FIG. 4 is a partial cross sectional view of the reservoir of FIG. 3 taken in the direction of arrows 4—4.

Referring now to FIGS. 1, 2, 3, and 4, reservoir system 11 also includes temperature probe 118. As shown in FIG. 4, probe 118 is positioned in the interior of reservoir 10 and consists of thermocouple 124 which is attached to and suspended from rod 120. Rod 120 hangs through an aperture (not shown) in top lid 125 of reservoir 10 to position thermocouple 124 in fluid 12 in lower portion 9. Rod 120 includes suitable electrical conductors to convey the signal from thermocouple 124 to controller 102.

Figure 5:
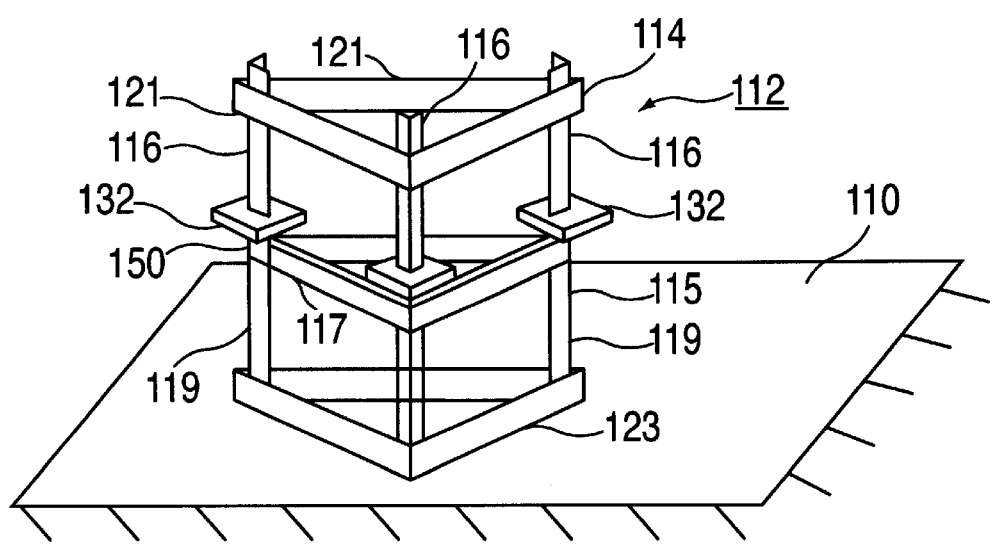
FIG. 5 is a pictorial representation of the reservoir support structure of FIG. 3 showing the pivot blocks.

Referring now to FIGS. 1, 2, 3, 5, 6 and 7, as shown in FIG. 3 and 5 reservoir 10 is supported above ground 110 by support structure 112. Structure 112 is designed with features that allow the change in mass of fluid 12 in reservoir 10 to be readily determined by scale 154 and controller 102. Structure 112 includes cradle 113 that cradles lower portion 9 of reservoir 10, supporting substantially all the weight of reservoir subsystem 11 and fluid 12. Cradle 113 is constructed of steel. Structure 112 includes upper base 114 and lower base 115. Cradle 113 attaches to and rests on upper base 114, which is positioned below cradle 113. Upper base 114 is positioned above and rests on lower base 115, separated from lower base 115 by three pivot blocks 132. Lower base 115 rests on ground 110. In this manner, support structure 112 is constructed such that substantially all the weight of reservoir subsystem 11 and fluid 12 is borne by the series combination of cradle 113, upper base 114, pivot blocks 132 and lower base 115.

Upper base 114 includes a plurality of substantially vertical legs 116. In FIG. 5, three substantially vertical legs 116 are shown positioned in a triangle configuration (i.e., with each leg at one of the three vertices of an equilateral triangle lying in a horizontal plane). This positioned is maintained by one horizontal level of cross bracings 121 positioned substantially at the horizontal midpoint of each leg 116 and by the attachment of the upper portion of each leg 116 to cradle 113.

Similar to upper base 114, lower base 115 includes three substantially vertical legs 119 positioned in a triangle configuration. Each leg 119 is substantially vertically aligned with one of the three legs 116 of upper base 114. The triangle configuration of legs 119 is maintained by two horizontal levels of cross bracings: Two cross braces 117 are positioned at the upper end of each leg 119 and connect to the upper end of each leg 119 at the apex of a horizontal equilateral triangle formed by braces 117. Two cross braces 123 are positioned at the lower end of each leg 119 and connect to the lower ends of leg 119 at the apex of a horizontal equilateral triangle formed by braces 123. Cross bracings 123 rest on ground 110 and contribute to the stability of structure 112.

Figures 6, 7:
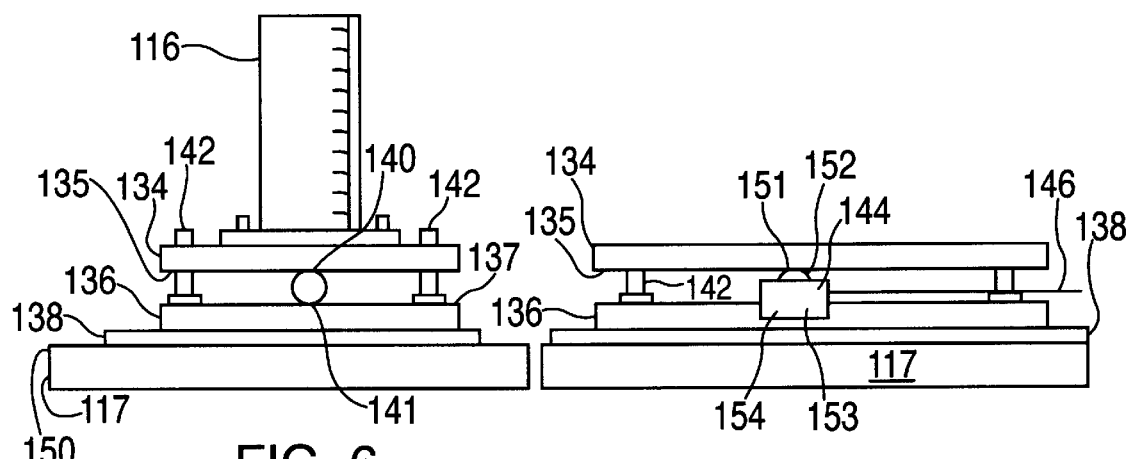
FIG. 6 is a plan view of a pivot block from FIG. 5 having a ball between the plates.
FIG. 7 is a partial cross sectional view of a pivot block from FIG. 5 having a load cell between the plates.

Referring now to FIGS. 5, 6 and 7, as shown in FIG. 5 upper base 114 and lower base 115 of support structure 112 are connected via pivot blocks 132. Each of the three pivot blocks 132 are vertically aligned with an associated pair of vertically aligned legs 116 and 119. In particular, the joining of a pair of cross bracings 117 with each leg 119 forms more stable platforms 150 for pivot blocks 132.

Referring now to FIGS. 5 and 6, each pivot block 132 includes upper plate 134, lower plate 136, guide posts 142 and vibration mount 138. Two pivot blocks include ball 140 (FIG. 6) and one pivot block 132 includes load cell 144 (FIG. 7), for measuring mass, in the place of ball 140. Each plate 134 and 136 is square shaped, about 1.0 cm thick and 10 cm long on each side of the square. Plates 134 and 136 are constructed of any suitable durable material, such as stainless steel. Each upper plate 134 is positioned below and is fixedly attached to an associated leg 116 by means of bolts or other suitable fasteners. Each lower plate 136 rests on an associated vibration mount 138, which in turn rests on the associated platform 150 formed by associated cross braces 117. Vibration mount 138 consists of a square section of 1.0 cm thick rubber or other suitable material with vibration dampening properties. For stability, the size of vibration mount 138 is preferably at least as big as plate 138 resting on it.

Each plate 134 is positioned substantially horizontally and includes a substantially flat surface 135 that also is positioned substantially horizontally. Each lower plate 136 is positioned substantially horizontally and includes a substantially flat surface 137 that also is positioned substantially horizontally. Each lower plate 136 is positioned below its associated upper plate 134 and two plates 136 are separated from this upper plate 134 by ball 140 and one by load cell 144.

Each ball 140 is substantially spherical in shape and is made of stainless steel or other suitable material. Flat surface 135 of upper plate 134 rests on ball 140, which in turn rests on flat surface 137 of lower plate 136. Flat surface 137 of lower plate 136 includes a small depression or divot 141 to provide a permanent, fixed location for the associated ball 140 or load cell 144. Load cell 144 has a substantially hemispherical upper surface 151 that attaches to a main body 153. Body 153 contains the load beam (not shown) that actually measures the mass bearing down on load cell 144. Preferably load cell 144 is the same height as the diameter of ball 144, or suitable adjustments are made to the thickness of the plate 134 and/or plate 136 associated with load cell 144 to accommodate any differences in vertical dimensions that would upset the symmetry of support structure 112. The arrangement with balls 140 means that upper plate 134 (and hence upper base 114, cradle 113 and reservoir 10) is free to move in a horizontal plane by rolling ball 140 between flat surface 135 of upper plate 134 and flat surface 137 of lower plate 138. The arrangement with load cell 144 means that upper plate 134 is free to move in a substantially vertical plane to press on hemispherical surface 151 at the point 152 where surface 151 contacts surface 135.

Horizontal movement of each pivot block 132 is limited by guide posts 142. Each pivot block 132 has at least one and preferably two or more substantially vertically oriented guide posts 142 that are fixedly connected to one plate 134 or 136 and pass through an aperture (not shown) in the other respective plate 138 or 134, with the aperture being of sufficient diameter with respect to the diameter of guide post 142 to keep post 142 from binding upper and lower plates 134 and 138.

The symmetrical design of support structure 112 described above results in the mass of fluid 12 and reservoir subsystem 11 (including reservoir 10) resting equally on balls 140 and load cell 144. Since each of the two balls 140 bears substantially the same weight as load cell 144, controller 102 multiplies by a factor of three the weight scale 154 reports is borne by load cell 144 to determine the overall mass.

Figure 8:
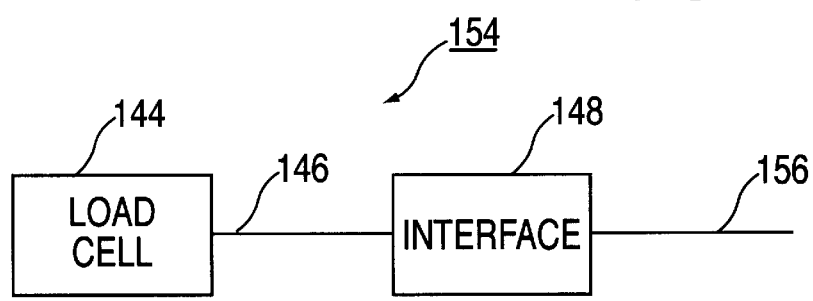
FIG. 8 is a block diagram of the reservoir scale.

Referring now to FIGS. 7 and 8, scale 154 includes interface 148 and cables 146 and 156. Interface 148 is connected to load cell 144 by signal cable 146. Load cell 144 generates a signal proportional to the mass impressed upon it. This signal is transmitted via cable 146 to interface 148. Interface 148 converts this signal into a form suitable for sending to controller 102 via cable 156.

One alternative to weighing reservoir subsystem as it rests on ground 110 is to suspend or hang reservoir subsystem 11 from one or more points (not shown) of a suitable superstructure (not shown), with one or more point (if similar symmetrical construction is used) or points equipped with scales similar to scale 154.

Referring now to FIGS. 1, 3 and 4, cooling system 80 returns fluid to reservoir 10 via pipe 81. Pipe 81 attaches to exterior surface 130 of reservoir 10 at the top of upper portion 7. Pipe 81 attaches to stand pipe 158 through an aperture (not shown) in the top of reservoir 10. Stand pipe 158 extends vertically downward into lower portion 9 and terminates in an angled opening positioned to send fluid 12 swirling across the bottom interior surface f conical lower portion 9 without introducing air into fluid 12.

Test Pump, Test Pump Drive Motor and Test Flow Meter Components

Figure 9:
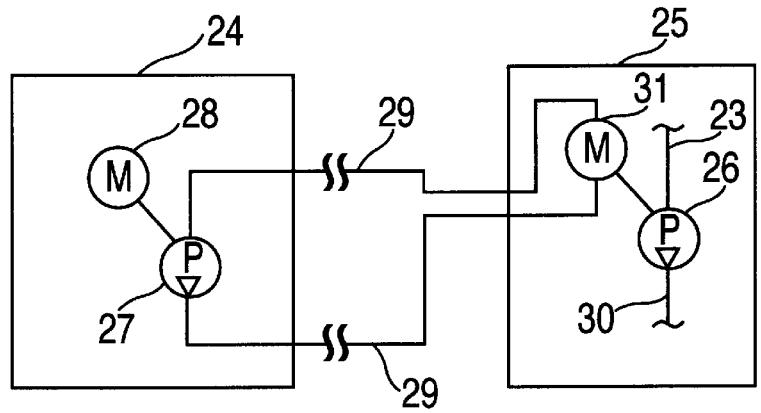
FIG. 9 is a block diagram of the hydrostatic drive separating the test pump and its associated drive motor of FIG. 1.

Referring now to FIGS. 1, 2 and 9, test pump 26 is driven directly by hydraulic motor 31. Hydraulic motor 31 is coupled via hydraulic fluid lines 29 to hydraulic drive pump 27. Hydraulic drive pump 27 is driven by motor 28, which is a constant speed AC motor connected to and controlled by controller 102. Drive pump 27 is a variable displacement pump having the pitch of its swash plate (i.e., rotors) controlled by controller 102. Pump 27 pumps hydraulic fluid (not shown) through fluid lines 29 to and from hydraulic motor 31. In turn, hydraulic motor 31 is directly coupled to test pump 26.

Hydraulic coupling through fluid lines 29 between variable displacement hydraulic drive pump 27 and hydraulic motor 31 provides a convenient means for changing and controlling the speed of test pump 26, under the control of controller 102. This arrangement also isolates test system 100 from noise and vibrations generated by motor 28 and by drive pump 27. With hydraulic coupling, motor 28 and associated pump 27 can readily be located a considerable distance from the other components of test system 100 to limit the vibrations transmitted from motor 28 and pump 27 to the remainder of test system 100 via the ground. With hydraulic coupling, motor 28 and pump 27 are readily placed in a separate space or room 24, away from room 25 that houses the remaining components of test system 100. Separate room 24 provides adequate space and adequate exhaust for the cooling system (not shown) for motor 28 without the need for room 24 to meet the more stringent cleanliness and humidity range required of room 25.

Figure 38:
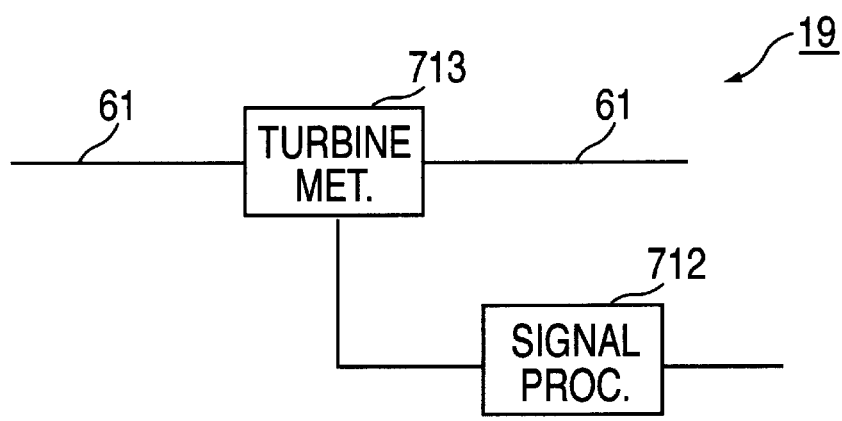
FIG. 38 is a schematic diagram of the main system flow meter used in the test system of FIG. 1.

From junction 60 at the outlet of test fixture 8, fluid flows through pipe 61 to clean up subsystem 70. Positioned before subsystem 70 are variable restriction 298 and test system flow meter 19. Valve 298 is a manual valve used to generate additional back pressure into test filter 6. The amount of restriction afforded by valve 298 is set by an operator before testing. Flow meter 19 is connected to controller 102 and measures the fluid flow rate through test filter 6. Referring now to FIGS. 1 and 38, there is shown a schematic diagram of flow meter 19, including turbine meter 713 and signal processor 712, which is connected to controller 102. Turbine meter 713 is connected to pipe 61 between valve 298 and cleanup subsystem 70. Turbine meter 713 includes a turbine (not shown) that revolves in response to fluid flowing through it, with its rate of revolution depending on the rate of flow of fluid through it. Turbine meter 713 includes electronics (not shown) that generate a signal representative of the rate of revolution of the turbine. This signal is conveyed to signal processor 712, which converts it to a form suitable for sending to controller 102. Controller 102 interprets the signal from signal processor 712 as the system flow rate.

Figure 39:
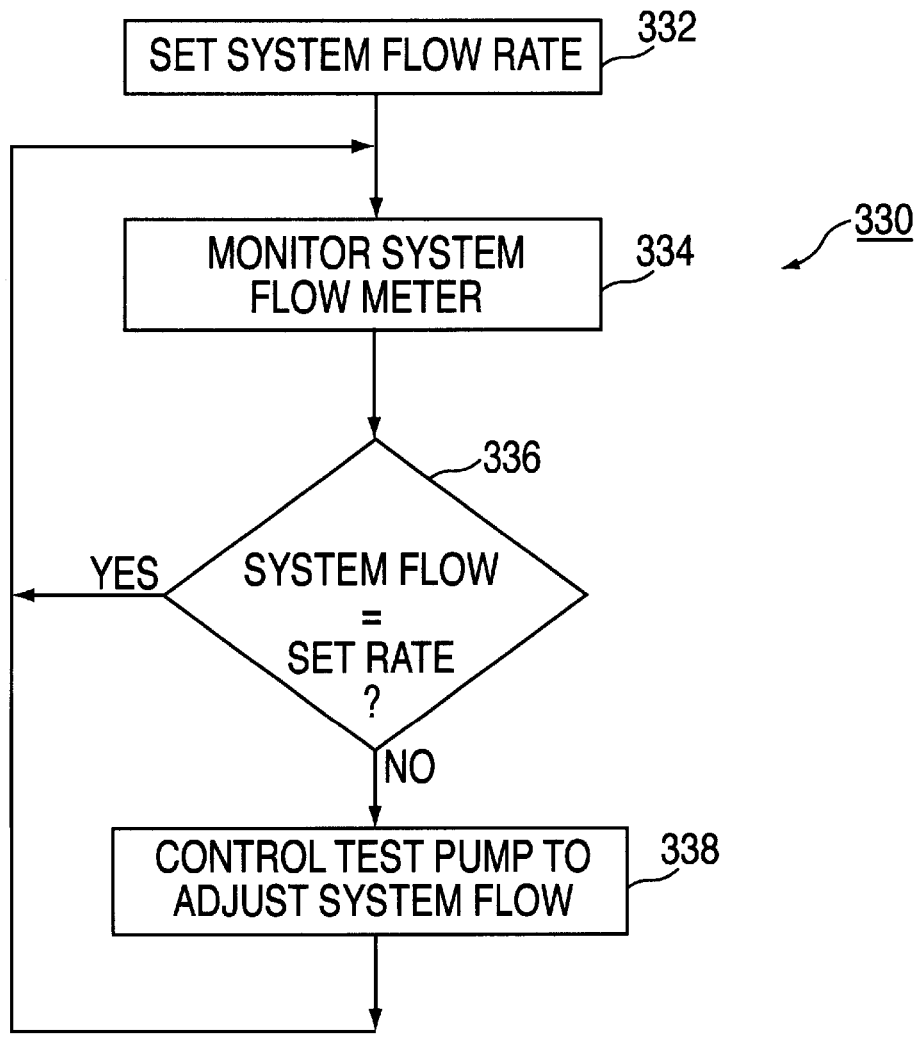
FIG. 39 is a flow chart of the control loop used by the controller to set and maintain the test system fluid flow rate.

Referring now to FIGS. 1, 2 and 39, in FIG. 39 there is shown a flow chart depicting control loop 330 used by controller 102 to maintain the desired fluid flow rate through test filter 6. In step 332 the test system flow rate is set. The rate can be chosen manually by an operator (not shown) at computer 161 (FIG. 14) or under control of software as a parameter in a test being run automatically by test system 100.

In step 334 controller 102 monitors flow meter 19 to determine the present flow rate. Next in step 336 controller 102 determines whether the flow rate is within an acceptable range of the desired rate. If so, controller 102 loops back to step 334. If not, in step 338 controller 102 controls the rotor pitch on drive pump 27 to alter, as required, the flow rate imparted to the fluid by test pump 26.

Test Fixture, Test Fixture Pressure Monitor and Test Fixture Vibration Monitor Components Referring now to FIGS. 1 and 2, preferably test fixture 8 is the same or substantially similar to the assembly that houses fluid filter 6 in actual use a machine or system (not shown). Using the same assembly is important to duplicate the conditions under which filter 6 may leak or otherwise be bypassed (e.g., due to back pressure caused by contaminants clogging filter 6).

Figure 11:
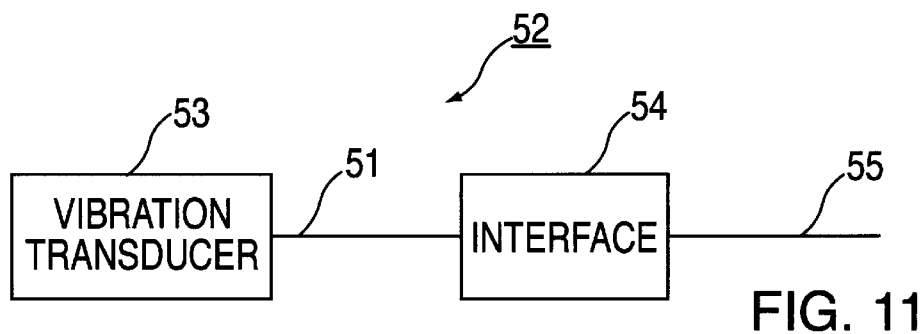
FIG. 11 is a block diagram of vibration monitoring accelerometer 52 of the test system of FIG. 1.

Referring now to FIGS. 1, 2 and 11, in FIG. 11 there is shown a block diagram of the components of vibration monitor 52. Monitor 52 includes a transducer 53, such as an accelerometer, for sensing vibrations and producing a signal representative of the sensed vibrations. Transducer 53 is attached to test fixture 8 by adhesive, magnet, tape, cable tie, or other suitable means adapted to the particular shape and material composition of test fixture 8. Monitor 52 also includes interface 54 that is connected to transducer 53 by cable 51 and to controller 102 by cable 55. Interface 54 receives a signal from transducer 53 representative of the vibrations sensed by transducer 53 and converts this signal into a form suitable for sending over cable 55 to controller 102.

Knowledge of the vibration of test fixture 8 is important for three main reasons. First, should various conditions (e.g., varying fluid flow rate through filter 6 and fixture 8 or fluid pressure fluctuations due to pump 26) cause test fixture 8 to vibrate excessively (e.g., at a resonant frequency), filter 6 may be made to shake lose previously trapped contaminants in a manner that skews the results of the testing. Monitoring vibrations of test fixture 8 allows such occurrences to be detected and noted in test reports.

Second, in testing filter 6 it may be desirable to duplicate the actual operating conditions of test filter 6 to such a degree of accuracy that the test even mimics the vibrations conveyed to filter 6, including any resonant frequencies of the actual filter housing simulated by test fixture 8. This test application requires using the actual filter housing as test fixture 8 and mounting test fixture 8 such that it exhibits substantially the same vibration and other movement characteristics of the actual filter housing.

Third, a test may require determining how filter 6 performs at a resonant frequency of the filter 6 and fixture 8 combination. With this test, test system 100 would first determine the resonant frequency (if any) of the filter 6 and fixture 8 combination, then operate test system 100 so as to produce such resonance for a particular period of time or until certain test criteria are achieved.

Referring now to FIGS. 1 and 2, the pressure at the inlet of test fixture 8 and the pressure drop across test fixture 8 are monitored by test fixture pressure monitor subsystem 56. Subsystem 56 is connected to controller 102 by cable 49 and is connected by suitable pipes to the inlet and outlet of test fixture 8. Subsystem 56 includes pressure monitoring transducer 57 connected to the inlet of test fixture 8 for monitoring the pressure of the fluid at the inlet and differential pressure monitoring transducer 58 connected to the inlet and outlet of test fixture 8 for monitoring the drop in pressure across fixture 8. Transducers 57 and 58 are any suitable devices capable of measurements of sufficient accuracy and capable of transmitting to controller 102 via cable 49 signals indicative of the pressures read.

Contaminant Monitor Subsystem Component

Referring now to FIGS. 1, 2, 12 and 13, in FIG. 1 contaminant monitor subsystem 34 is shown to include upstream monitor 46 for monitoring the contaminant level of fluid diverted from junction 32 at the inlet of test fixture 8 and downstream monitor 50 for monitoring the contaminant level of fluid diverted from junction 60 at the outlet of test fixture 8.

Referring now to FIG. 1, preferably the portion of fluid diverted at junction 32 towards contamination monitoring subsystem 34 is a relatively small, predetermined, precise portion of the total fluid flowing into junction 32. Diverting a relatively small percentage of fluid minimizes the inaccuracy introduced into the measurement of the filtering ability of filter 6 caused by not subjecting filter 6 to all of the contaminants in the contaminated fluid 16 injected at junction 20. Diverting a relatively precise portion of the total fluid allows the measurements by the contamination monitoring subsystem 34 to be more accurately converted into a measurement of the contaminants in the non-diverted fluid that is filtered by test filter 6.

From the outlet of test fixture 8, fluid path 59 conveys fluid to junction 60. From junction 60 most of the fluid from the outlet is conveyed by fluid path 61 to cleanup subsystem 70 and a relatively small, precise, predetermined portion of the fluid is diverted and conveyed to inlet 39 of downstream monitor 50 by fluid path 62. The reasons for diverting a small, precise, predetermined portion of the fluid to inlet 39 of downstream monitor 50 are the same as for upstream monitor 46.

Figure 12:
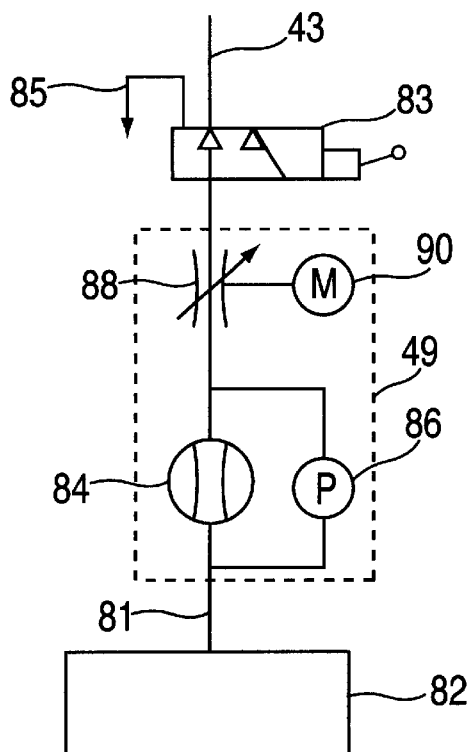
FIG. 12 is a schematic diagram of the particle counter, flow measuring apparatus and flow control components of contamination monitor subsystem of FIG. 1.

Referring now to FIGS. 1, 2 and 12, preferably monitors 46 and 50 are constructed substantially the same for ease of design, maintenance, repair and replacement. FIG. 12 shows a detailed diagram of the components of monitors 46 and 50 and FIG. 13 shows the control system architecture 98 of monitors 46 and 50. Each monitor 46 and 50 includes particle counter 82, capillary tube 84, differential pressure monitor 86, adjustable valve 88, valve motor 90 and manual drain valve 83. For monitors 46 and 50, fluid flows into each particle counter 82 via respective pipes 35 and 62. Each particle counter 82 is connected to and controlled by controller 102. Each particle counter 82 is connected to controller 102 by cable 91. From particle counter 82, in each monitor 46 and 50 fluid flows via pipe 81 into capillary 84. Across capillary 84 is connected differential pressure monitor 86. Pressure monitor 86 is connected via cable 87 to controller 102. From capillary 84 fluid flows through variable valve 88 to manual drain valve 83. Variable valve 88 is controlled by motor 90, which is connected to and controlled by controller 102. Motor 90 is connected to controller 102 via cable 89.

Manual drain valve 83 is a two position manual valve that can be positioned manually to send fluid into drain 85 for collecting in a sample glass (not shown) for analysis and/or calibration. In normal operation valve 83 is positioned to allow fluid to flow instead to fluid path 43.

Monitors 46 and 50 each contain two precision devices that work together to allow accurate and substantially real time monitoring of the contaminant level in the fluid and flow meter 49. Suitable particle counters 82 are available commercially. Preferably particle counters 82 are model LB-1020 available from Met One Company.

Flow monitor 49 is formed by capillary tube 84, adjustable valve 88, differential pressure monitor 86, all under the control of controller 102. For a particular flow rate through test fixture 8 and filter 6, flow monitor 49 maintains a substantially constant, relatively precise, measurable flow of fluid through particle counter 82 so that controller 102 can convert knowledge of the particles counter and the flow rate through capillary 82 into a measure of contaminant concentration.

To allow controller 102 to measure the fluid flow through particle counter 82, capillary 88 is calibrated such that the pressure drop across it is in a known relationship to the rate of flow of fluid through it over a particular range of flow rates and temperatures of the fluid. Pressure monitor 86 measures this pressure drop and conveys the information to controller 102 via cable 87.

Proper operation of flow monitor 49 is jeopardized by contaminants present in the fluid. These contaminants can adhere to portions of valve 88, significantly affecting the flow of fluid through capillary 84. To minimize contaminant adhesion to valve 88, preferably valve 88 is a needle valve. To further minimize contaminant adhesion, valve 88 is positioned vertically such that the needle (not shown) of valve 88 is substantially vertically oriented.

In response to periodic partial obstructions of valve 88, controller 102 must order motor 90 to make fairly precise alterations to the flow through valve 88. For precision, preferably motor 90 is a stepper motor. Suitable stepper motors include model Hi-2.200210 AX 80, available from Oregon Micro Company.

Figures 40, 41:
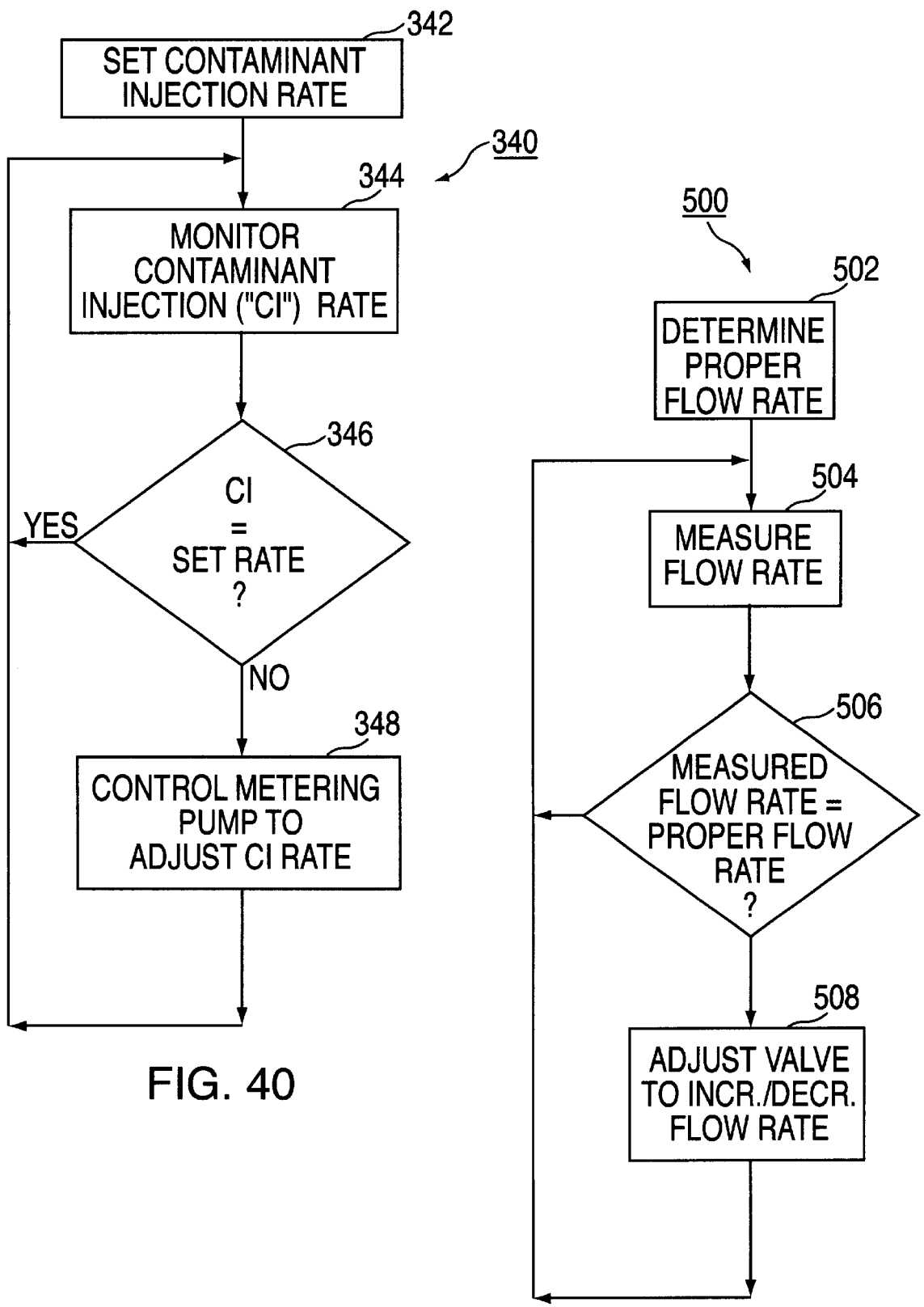
FIG. 40 is a flow chart of the control loop used by the controller to set and maintain the rate of flow of contaminated fluid into test filter 6.
FIG. 41 is a flow chart of the control loop used by the controller to adjust the flow rate through the flow monitor of FIG. 12 in response to the measured flow rate.

Referring now to FIG. 41, there is shown a flow chart 500 that illustrates the control loop used by controller 102 to adjust the fluid flow through flow monitor 49. In step 502 controller 102 determines the proper flow rate through flow monitor 49. This rate is preferably 100 mL/min. Next in step 504 controller 102 converts the pressure measured by pressure monitor 86 into a value representative of the flow rate through capillary 84. Next in step 506 controller 102 determines whether this measured flow rate is within an acceptable range of the desired flow rate. If it is, then controller 102 loops back to step 504. If it is not, then in step 508 controller 102 sends control signals to stepping motor 90 to increase or decrease the opening of needle valve 88, as appropriate, to respectively increase or decrease the flow rate. Then controller loops back to step 504.

Referring now to FIGS. 2, 12 and 13, at start up controller 102 is unaware of the position of valve 88. To give controller 102 an initial indication of the position of valve 88, use can be made of either upper limit switch 92 or lower limit switch 94, both of which are attached to valve 88. Switches 92 and 94 are connected by respective cables 93 and 95 to controller 102. Upper limit switch 92 is connected to valve 88 so as to signal controller 102 via cable 93 when motor 90 has opened valve 88 as far as possible (e.g., by withdrawing the needle (not shown) of valve 88 from its orifice (not shown) by the maximum desired amount). A similar function is performed by switch 94 and cable 95, but with respect to valve 88 being completely closed (e.g., by inserting the needle (not shown) all the way into the orifice(not shown) of valve 88).

When test system 100 is powered down in non-emergency fashion, preferably controller 102 orders valve 88 closed all the way so as to trigger the lower limit switch 94. Preferably valve 88 is closed all the way.

Referring now to FIG. 1, there are a few design choices for channeling the fluid that has passed through contaminant monitoring subsystem 34. In the preferred embodiment this fluid is conveyed by fluid path 43 to junction 20 at the inlet of test pump 26. Alternatively, this fluid could be returned to reservoir 10. Cost and complexity aside, the most accurate approach (not shown) would be to return fluid diverted from the inlet of test fixture 8 to this inlet downstream of junction 32. Similarly, the fluid diverted from the outlet of test fixture 8 would be reintroduced to this outlet downstream of junction 59.

Dilution Subsystem

Figure 16:
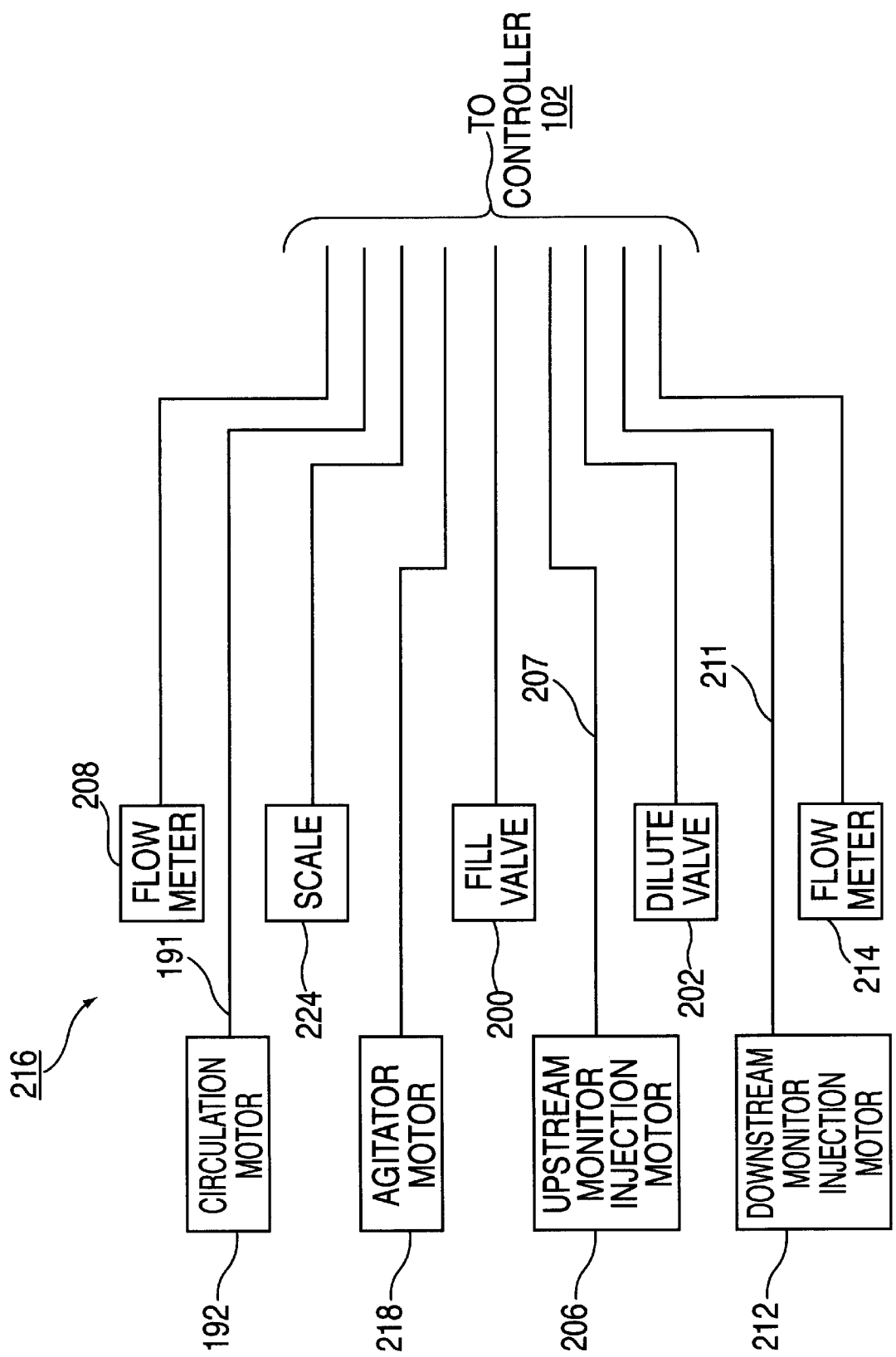
FIG. 16 is a block diagram of the connections between the controller of FIG. 2 and certain components of the dilution subsystem of FIG. 15.
Figure 17:
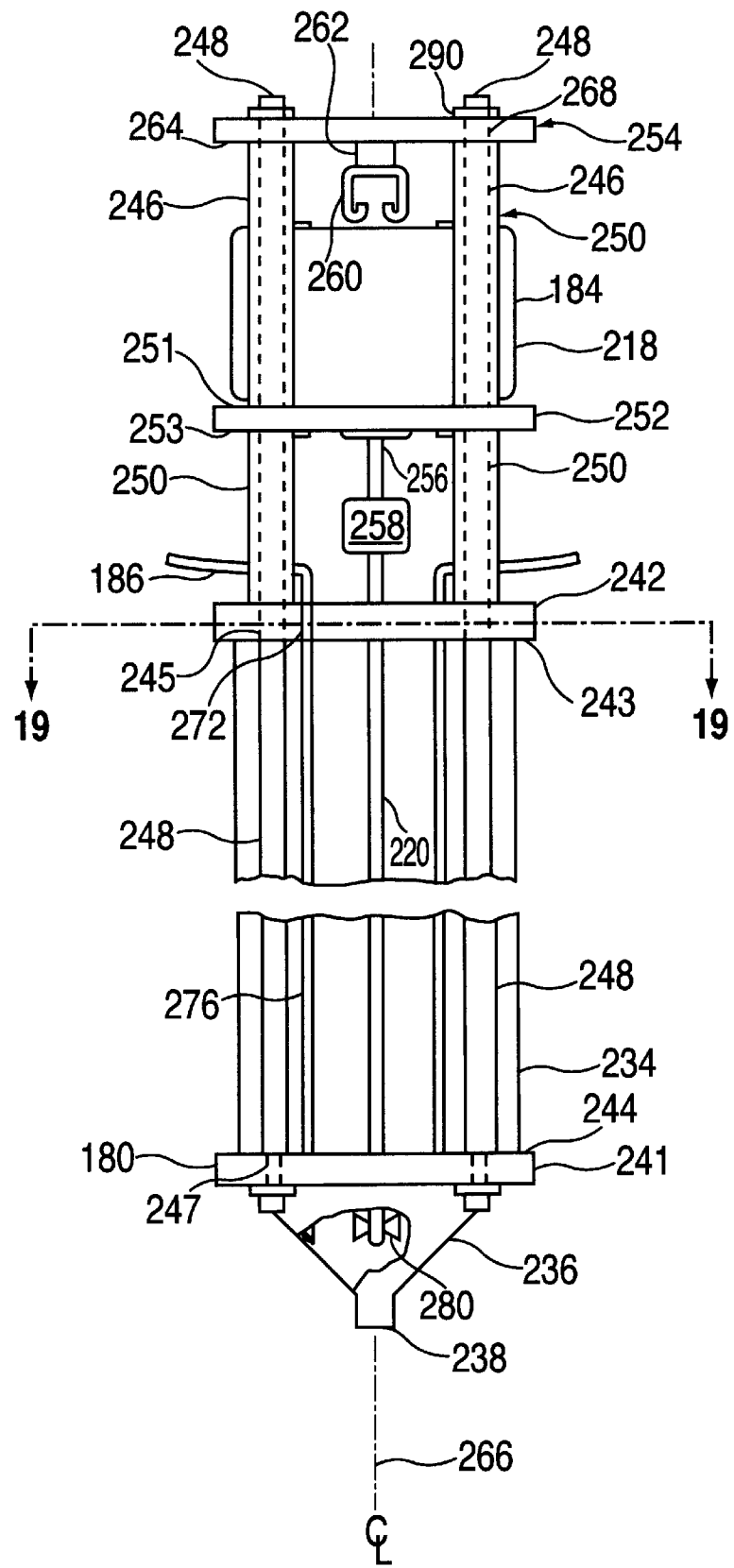
FIG. 17 is a front view of the reservoir and associate components of the dilution subsystem of FIG. 15.

Referring now to FIGS. 1, 2, 15, 16, 17, and 43, FIG. 15 is a schematic diagram of the fluid components of dilution subsystem 42, showing dilution reservoir 180 and associated agitator 184 and fill line 186, manual valve 188, circulation pump 190 and associated motor 192, check valve 194, filter 196, variable valve 198, valve 200, valve 202, metering pump 204 and associated motor 206, flow meter 208, metering pump 210 and associated motor 212 and flow meter 214. FIG. 16 shows the control system architecture 216 of dilution subsystem 42, showing the connections between components of dilution subsystem 42 and controller 102. FIG. 17 is a pictorial representation of dilution reservoir 180 and certain components attached to reservoir 180.

Referring now to FIGS. 1, 2, 15 and 16, reservoir 180 contains a supply of substantially clean fluid 44. Fluid 44 should meet AS 4059, Class 0 or better. Fluid 44 is supplied to reservoir 180 by cleanup subsystem 70 via pipe 78. As previously mentioned, fluid 44 preferably contains a lesser degree of contaminants than the substantially clean fluid 12 that fills reservoir 10, since any contaminants in fluid 44 can skew the contamination measurements of monitors 46 and 50.

Pipe 78 attaches to valve 200, which is normally closed. From valve 200, the fluid is conveyed via pipe 222 through fill valve 198 and clean up filter 196 to fill line 186 and into reservoir 180. Valve 200 is controlled by controller 102. Fill valve 200 can be either electrically operated or pneumatically operated. Variable valve 198 acts to control the rate at which reservoir 180 is filled with fluid 44. Clean-up filter 196 serves to supplement cleanup subsystem 70.

Referring now to FIGS. 1, 2, 15 and 17, from reservoir 180 fluid 44 flows through manual shut off valve 188 to the inlet of recirculating pump 190. Pump 190 is driven by motor 192, which is connected to and controlled by controller 102 via cable 191. Motor 192 is any suitable motor, such as a continuous speed AC motor. The outlet of pump 190 is connected through check valve 194 to junction 228, which is in pipe 222 between clean up filter 196 and valve 198. Fluid passing along this path passes through filter 196 to junction 226. From junction 226 fluid passes either into reservoir 180 or through shutoff valve 202.

Shutoff valve is connected to and controlled by controller 102, and can be either electrically or pneumatically operated. Shutoff valve 202 is normally closed, so that fluid from pump 190 normally recirculates into reservoir 180.

When valve 202 is open, fluid flows from pump 190 to junction 230, where the fluid is diverted into two flow paths, one to the inlet of upstream metering pump 204 and one to the inlet of downstream metering pump 210. Pumps 204 and 210 are driven by respective motors 206 and 212, which are connected to and controlled by controller 102 via respective cables 207 and 211. Motors 206 and 212 can be any suitable variable speed motor. From the outlet of metering pump 204, fluid passes through flow meter 208 to line 40, which conveys the fluid through check valve 38 to mixing chamber 36 at the inlet of upstream monitor 46. From the outlet of pump 210, fluid passes through flow meter 214 to line 41, which conveys the fluid through check valve 39 to mixing chamber 37 at the inlet of downstream monitor 50.

Test system 100 determines the rate of flow of fluid 44 from reservoir 180 to contamination monitors 46 and 50 using flow meters 208 and 214, respectively. Flow meters 208 are constructed substantially similar to flow meter 49 (shown in FIG. 12) and are controlled by controller 102 substantially as shown in flow chart 500 (FIG. 41).

Preferably controller 102 operates dilution subsystem 42 to inject fluid 44 into the inlets of monitors 46 or 50 whenever the contamination measurements reported by monitors 46 or 50 to controller 102 are at or near the upper range of accurate measurements by monitors 46 or 50. In operation, controller 102 adjusts the contamination measurements reported by monitors 46 or 50 by the rate, if any, of the flow of fluid 44 into the inlets of monitors 46 or 50 reported to controller 102 by respective flow meters 208 and 214.

Figure 43:
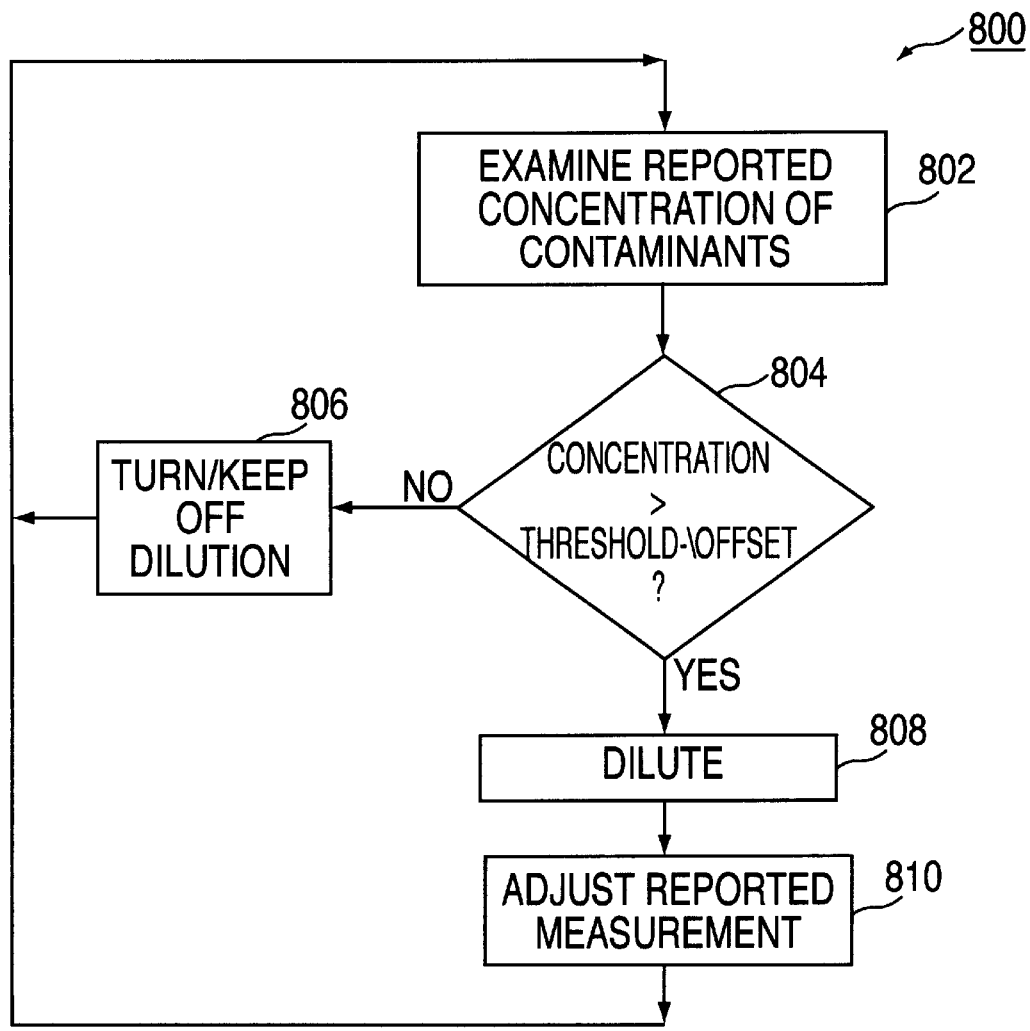
FIG. 43 is a flow chart of the control loop used by the controller to control the dilution subsystem and adjust the contamination measurements reported by the upstream and downstream monitors.

Controller 102 accomplishes these activities by means of the software program 800 shown in FIG. 43. In step 802 controller 102 examines the contaminants concentrations reported by respective upstream and downstream contamination monitors 46 and 50. In step 804, controller 102 compares these reported measurements to the upper measurement threshold of the monitors 46 and 50. Preferably, controller 102 compares the reported measurements to a predetermined amount that is less than the upper measurement thresholds by a predetermined offset, so that controller 102 can activate the dilution subsystem 42 before the contaminant concentrations reach the upper measurement thresholds.

If the reported concentration does not exceed the offset threshold, in step 806 controller 102 keeps off (or turns off, as the case may be) the flow of fluid to that particular monitor 46 or 50 (by proper operation of valve 202 and with metering pumps 204 and 210 not operating), then loops back to step 802. If the reported concentration does exceed the offset threshold, in step 808 controller 102 orders dilution subsystem 42 to provide a predetermined rate of flow of fluid to that particular monitor 46 or 50 (by proper operation of valve 202 and metering pumps 204 or 210). Then in step 810 controller 102 adjusts any future measurements reported by monitors 46 or 50 to take into account the rate of flow of dilution fluid measure by respective monitors 208 and 214, then loops back to step 802.

Referring now to FIGS. 15, 16, 17 and 18, in FIG. 17 there is shown a front view of reservoir 180 and certain other components of dilution subsystem 42 associated with reservoir 180. Reservoir 180 consists essentially of a vertically-oriented hollow cylindrical column 234 suitable for storing fluid 44. At the bottom of column 234 is attached in fluid communication a funnel-shaped hollow base 236 having narrow exit 238 at its bottom that connects via pipe 240 to manual valve 188. Both column 234 and funnel base 236 have smooth interior surfaces. This design of reservoir 180 minimizes horizontal surfaces on which contaminants could settle.

When dilution reservoir 180 is empty or near empty it is necessary for controller 102 to detect these condition and order it filled with more fluid. Controller detects these conditions using scale 224, connected to controller 102, to weigh reservoir 180, fluid 44 contained in reservoir 180, and other components of dilution subsystem 42 attached to reservoir 180. Controller 102 calculates the volume of fluid contained in reservoir 180 from the known density of fluid 44 and from the mass measured by scale 224. Note that were scale 224 sufficiently accurate, controller 102 could calculate the change in weight read by scale 224 with respect to time and thereby derive the rate of fluid flow from reservoir 180 based on the known density of the fluid.

To minimize the expense of scale 224, dilution subsystem 42 is constructed such that reservoir 180 and attached components are suspended essentially from beam 260 of test system housing (not shown) at a single point, with a single load cell 262 placed between that point and beam 260 such that reservoir 180 and attached components compress load cell 262 against beam 260.

To support reservoir 180 and associated components, dilution subsystem 42 includes funnel base 236, cylinder top plate 242, agitator motor support plate 252, suspension plate 254 and hanging rods 246. The top of reservoir cylinder 234 is capped by top plate 242. Top plate 242 is a flat, round plate having a diameter greater than that of cylinder 234 such that rim 243 protrudes beyond the exterior wall of cylinder 234. Rim 243 includes holes 245 (shown as dashed lines in FIG. 17) through which portions of hanging rods 246 can pass. Preferably there are four holes 245 spaced symmetrically around the perimeter of rim 243.

Funnel base 236 includes top portion 241 positioned at its top having rim 244 of substantially similar dimension and axially aligned with rim 244 of top plate 242. Rim 244 includes holes 247 (shown as dashed lines in FIG. 17) through which portions of hanging rods 246 can pass. Preferably there are four holes 247 spaced symmetrically around the perimeter of rim 244, with each hole 247 vertically aligned with an associated hole 245 in top plate 242. Reservoir cylinder 234 is clamped between top plate 242 and funnel base 236 by hanging rods 246. Suitable sealing means are provided to seal reservoir cylinder 234, funnel base 236 and top plate 242 in order to make reservoir 180 substantially leak proof.

Agitator motor base plate 252 supports agitator motor 218 of agitator 184 in a position above reservoir 180. Motor base plate 252 is positioned above and vertically aligned with top plate 242 and funnel base 236. Base plate 252 is separated from top plate 242 a distance sufficient to allow agitator motor drive shaft 256 to couple with stir rod 220 of agitator 184 by means of coupling 258. Base plate 252 is a square, flat plate having outer rim portion 253 with holes 251 (shown as dashed lines in FIG. 17) through which portions of hanging rods 246 can pass. Holes 251 are axially aligned with respective holes 245 and 247 in respective top plate 242 and top portion 241.

Suspension plate 254 is positioned above motor base plate 252, above the top portion of motor 118 and above beam 260 of the housing (not shown) of test system 100. Positioned between beam 260 and suspension plate 254 is load cell 262 of scale 224. Suspension plate 254 attaches to rods 246 and compresses load cell 262 against beam 260 with the mass of the components supported by rods 246, including reservoir 180 and fluid 44 it contains.

Suspension plate 254 is a square, flat plate having outer rim portion 264 with holes 268 (shown as dashed lines in FIG. 17) through which portions of hanging rods 246 can pass. Holes 268 are axially aligned with respective holes 251, 245 and 247 in respective motor suspension plate 252, top plate 242 and top portion 241 of funnel base 236.

Referring now to FIG. 17, for proper operation of scale 224, preferably the components suspended on load cell 262 and beam 260 are substantially symmetrical about vertical axis 266. In particular, there should be such symmetry for the centers of suspension plate 254, motor suspension plate 252, top plate 242 and funnel base 236. Similarly, shaft 256 of agitator motor 218 and agitator rod 220 (and attached agitator propeller 280) should be vertically aligned with vertical axis 266, as should cylinder 234 and funnel base 236, including funnel exit 238.

Figure 19:
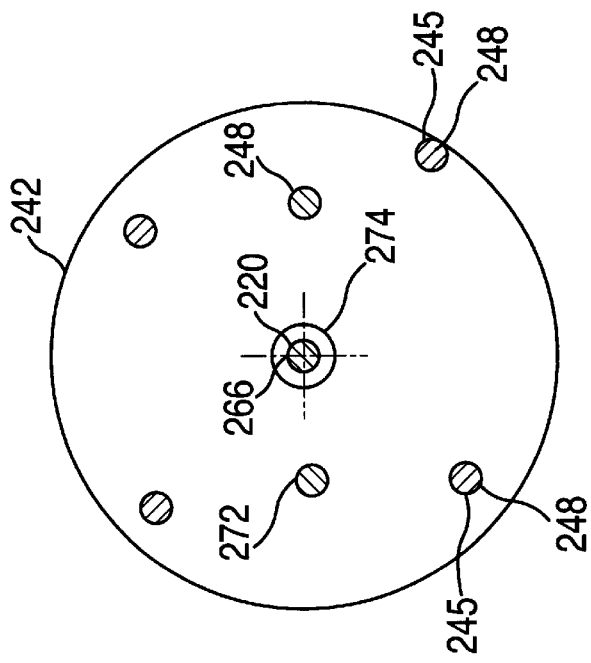
FIG. 19 is a cross section of the top plate in FIG. 17 taken in the direction of arrows 19–19.

Referring now to FIGS. 17 and 19, fill line 186 removably attaches via suitable fixtures to the top surface of top plate 242 at the location of hole 272 (shown as dashed lines in FIG. 17). Hole 272 communicates with stand pipe 276. Stand pipe 276 removably attaches via suitable fixtures to the bottom surface of top plate 242 at the location of hole 272. Stand pipe 276 is a hollow pipe that is substantially vertically aligned and that extends from top plate 242 down into funnel base 236, terminating in a slant cut section (not shown).

As seen in FIG. 19, top plate 242 includes hole 274 through which can pass stir rod 220 of agitator 184. Hole 274 is aligned with axis 266 and of sufficient diameter to allow rod 220 to rotate freely. Top plate 242 also includes vent 248 that allows air to exit and enter reservoir 180 in response to fluid entering and exiting reservoir 180, respectively.

Agitator 184 mixes fluid 44 under control of controller 102. In particular, motor 218 turns its shaft 256 which in turn rotates rod 220 via coupler 258. Coupler 258 is a cylinder of rubber or other suitable materials, with holes (not shown) axially aligned with axis 266 into which the appropriate ends of shaft 256 and rod 220 could each be force fitted. At the bottom end of rod 220 is prop 280. Preferably rod 220 positions prop 280 in the proximity of funnel base 236 of reservoir 180.

Preferably motor 218 is electric to simplify the wiring and control of agitator 184. It would be well known to those skilled in the art to select appropriate parameters and other design considerations for agitator 184, such as the torque rating of motor 218, the shape of prop 280 and the speed of rotation of agitator rod 220 and the profile of such rotation over time.

Referring now to FIGS. 17 and 19, preferably each rod 246 consists of solid rod 248 having a diameter suitable for passing through holes 268, 251 and 247, and two hollow rod segments 250 used to space plates 242, 252 and 254. Each hollow rod segment 250 has a hollow interior through which solid rod 248 can pass and an exterior diameter larger than the diameter of holes 268 and 251. With this design, starting from the lower end of reservoir 180, each solid rod 248 can be threaded through hole 247, and hole 245, and then passed through two segments 250, with the first segment 250 placed between suspension plate 254 and motor base plate 252 and the second segment 250 placed between motor base plate 252 and top plate 242. To secure rods 246 in place, each end of each solid rod 248 is threaded, and these threaded ends are tightened with nuts 290.

Figure 18:
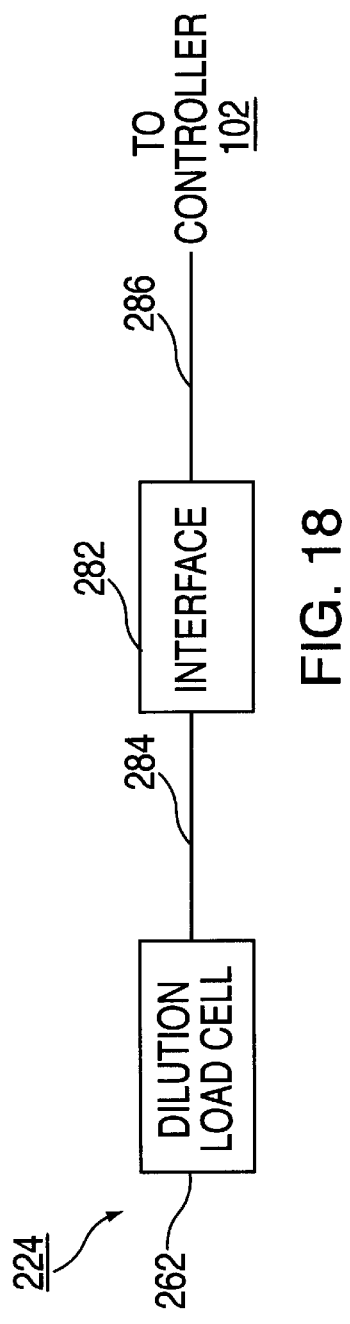
FIG. 18 is a block diagram of the scale associated with the load cell shown in FIG. 17.

Referring now to FIGS. 16, 17 and 18, in FIG. 18 there is shown a schematic diagram of scale 224. Scale 224 includes interface 282 that connects to load cell 262 via suitable cable 284. Load cell 262 produces a signal representative of the mass resting on it and transfers that signal to interface 282 via cable 284. Interface 282 converts this signal into a signal suitable for sending to controller 102 via cable 286.

Figure 20:
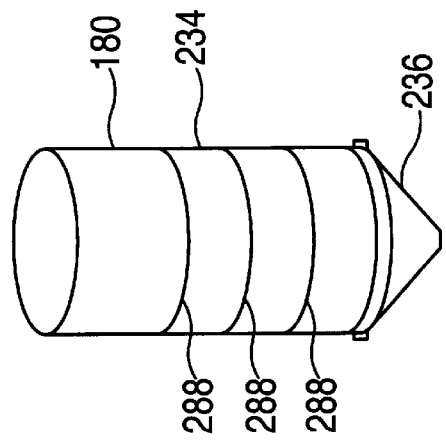
FIG. 20 is a simplified pictorial view of the reservoir of FIG. 15 showing the graduations of volume marked on the reservoir.

In FIG. 20 there is shown a simplified pictorial view of reservoir 180. Preferably cylinder 234 of reservoir 180 is constructed of clear or opaque glass or other suitable transparent or opaque material (e.g., clear or opaque plastic). In this manner an observer or operator (not shown) can view the fluid the level of fluid (not shown) in reservoir 180 to tell at a glance the operational status of reservoir 180 and dilution subsystem 42.

To aide in quantitative assessments, preferably cylinder 180 includes marks or graduations 288 on the surface of cylinder 234. For example, marks 288 could be painted on the exterior surface of cylinder 234 and calibrated to each indicate a liter of fluid (or any fraction or multiple of a liter). In the preferred embodiment these marks 288 are only used to correlate with the status indicated on monitor 162 and not to measure fluid flow rate or perform any other activities test system 100 performs automatically.

Clean Up Subsystem

Figures 21, 22:
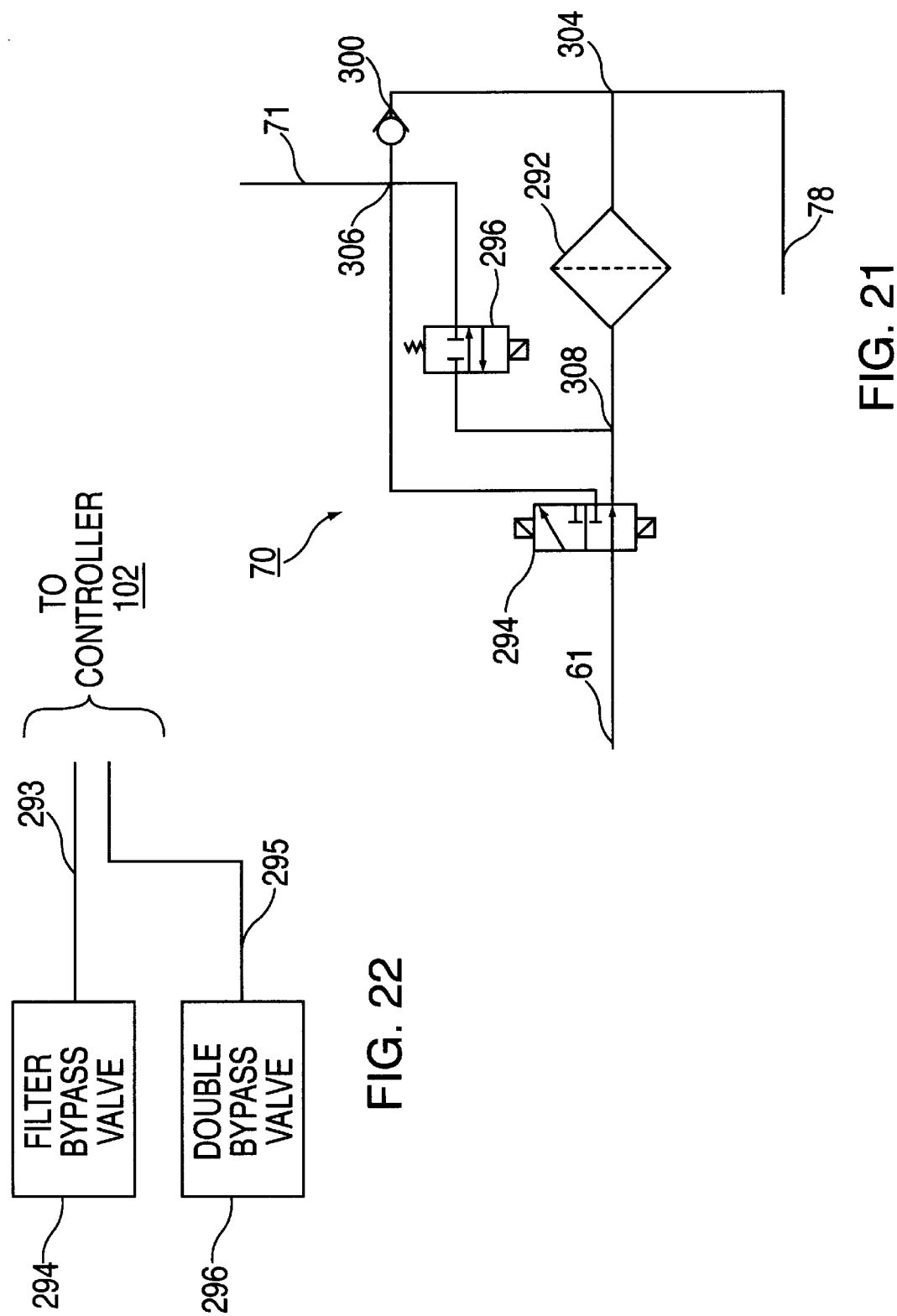
FIG. 21 is a schematic diagram of the clean up subsystem of FIG. 1.
FIG. 22 is a block diagram of the connections between the controller of FIG. 2 and certain components of the clean up subsystem of FIG. 21.

Referring now to FIGS. 1, 2, 21 and 22, FIG. 21 is a schematic diagram of the fluid components of cleanup subsystem 70, including cleanup filter 292, two way valve 294, shut off valve 296 and check valve 300. FIG. 22 is a block diagram of the connections between controller 102 and certain components 294 and 296 of cleanup subsystem 70.

In operation, cleanup subsystem 70 receives fluid from test fixture 8 via pipe 61. This fluid flows to filter bypass valve 294. Valve 294 has two positions and three connections and is connected to and controlled by controller 102 via cable 293. In one position valve 294 directs the fluid through cleanup filter 292 to junction 304. At junction 304 substantially most or all of the fluid flows through check valve 300 to junction 306. Some relatively small portion of the fluid can be made by controller 102 to flow from junction 306 through pipe 78 to dilution subsystem 42. Details of such flow are discussed in the Dilution Subsystem section.

In the other position, valve 294 bypasses cleanup filter 292, directing the fluid to junction 306. Note that in this second position the fluid from junction 306 is prevented by check valve 300 from entering the outlet of cleanup filter 292. The bypass of cleanup filter 292 is required by multi-pass tests and not by single pass tests.

One side effect of positioning valve 294 to bypass cleanup filter 292 is that dilution subsystem 42 is denied fluid at junction 304. To supply dilution subsystem 42 with substantially clean fluid, cleanup subsystem 70 includes double bypass valve 296. Valve 296 connects junction 306 to junction 308, which is positioned in the fluid path between valve 294 and cleanup filter 292. Valve 296 is connected to and controlled by controller 102 via cable 295. When valve 294 is positioned to bypass cleanup filter 292, controller 102 can order valve 296 to divert a relatively small portion of the fluid flowing through valve 294 from junction 306, through cleanup filter 292 to junction 304. From junction 304 the fluid is directed along path 78 to dilution subsystem 42. Note that no fluid flows from junction 304 through check valve 300.

Cleanup filter 292 can be any of a number of types of filters well known to those skilled in the art. The specifications required of filter 292 depend, of course, on the types of contaminants 17 being filtered by test filter 6. In particular, preferably cleanup filter 292 obtains a Filtration Ratio of 200 or greater for the smallest particle size of interest in the particular filter test, under all operating conditions specified for the filter test, and in addition is capable of maintaining a fluid cleanliness of AS 4059 class 1 or better at maximum rated flow for test system 100, when test filter 6 is not installed in test fixture 8.

Preferably filter bypass valve 294 air piloted and double bypass valve 296 is solenoid activated under control of controller 102. To operate valves 294 and 296, controller sends appropriate signals via respective cables 293 and 295 to the respective solenoids (not shown). An air source (not shown) sends the appropriate air pressure down pneumatic lines (not shown) to valve 294.

Contaminant Injection Subsystem

Figure 23:
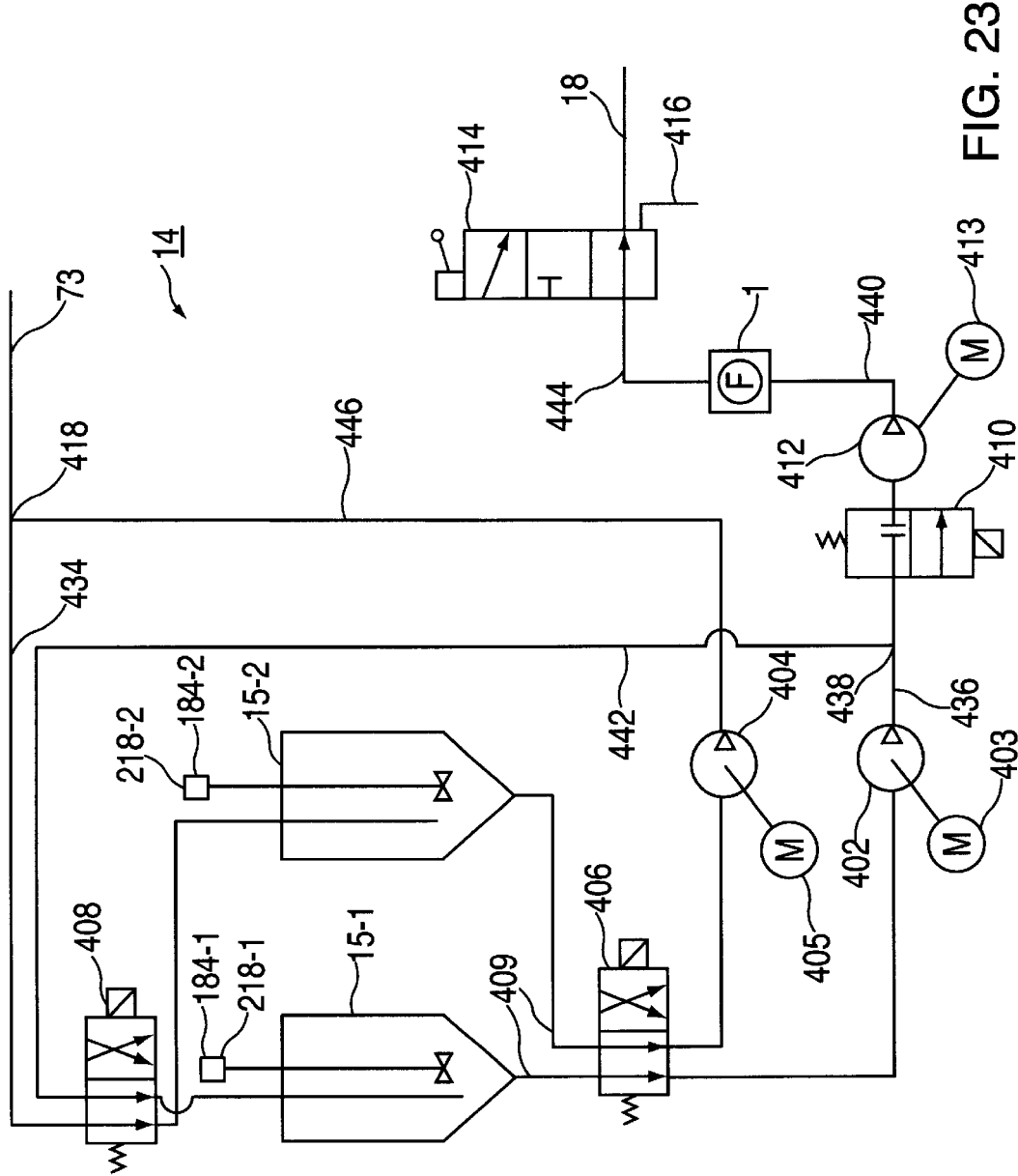
FIG. 23 is a schematic diagram of the contaminant injection subsystem of the test system of FIG. 1.
Figure 24:
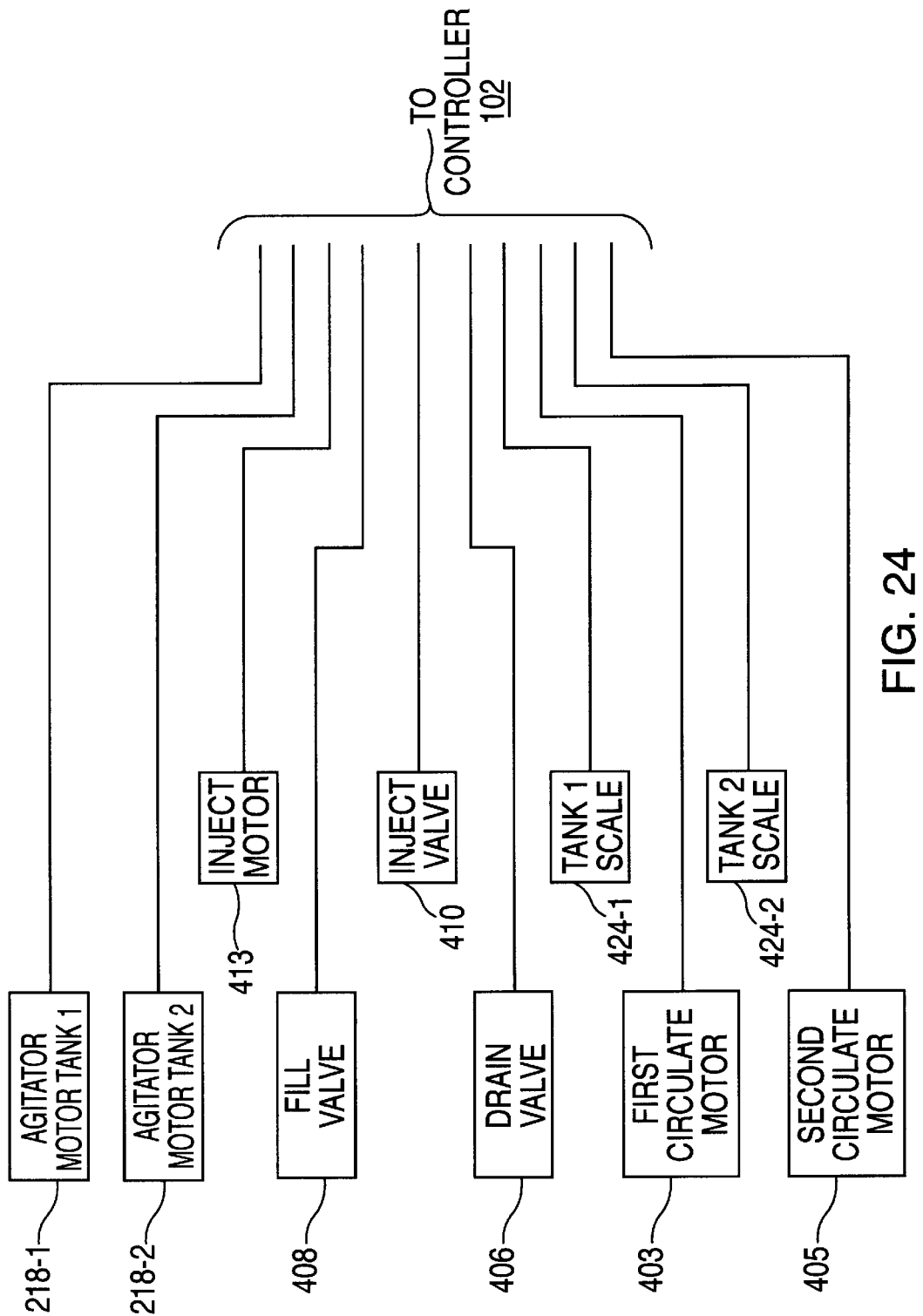
FIG. 24 is a block diagram of the connections between the controller of FIG. 2 and certain components of the contaminant injection subsystem of FIG. 23.
Figure 28:
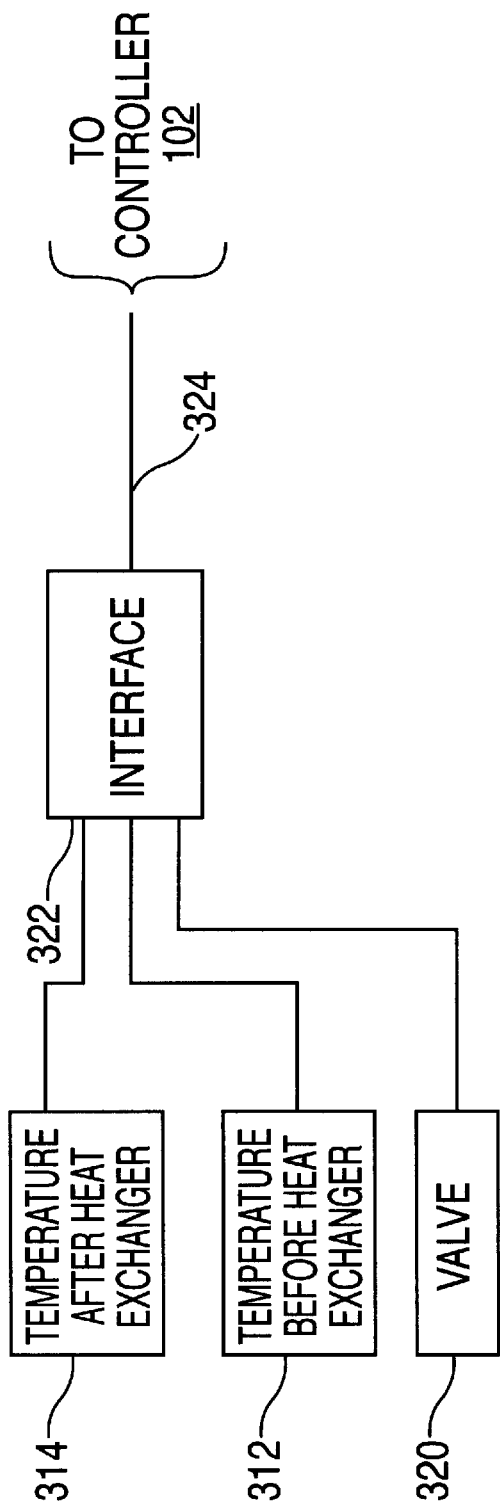
FIG. 28 is a block diagram of the connections between the controller of FIG. 2 and certain components of the cooling subsystem of FIG. 27.

Referring now to FIGS. 1, 2, 23, 24, 25, 26 and 38, FIG. 23 is a schematic diagram of the fluid components of contaminant subsystem 14, including contaminant reservoirs 15, fill valve 408, reservoir selection valve 406, first circulation pump 402 and associated motor 403, second circulation pump 404 and associated motor 405, injection valve 410, injection pump 412 and associated motor 413, flow meter 1 and manual valve 414. FIG. 25 is a top view of the top plate of reservoir 15 showing the opening for adding a precise charge of contaminants. FIG. 24 is a block diagram of the connections between controller 102 and certain components of contaminant subsystem 14. FIG. 26 is a block diagram of scale 424. FIG. 38 is a schematic diagram of flow meter 1.

Referring now to FIGS. 1 and 23, each reservoir 15 holds fluid 16 into which contaminants (not shown) from a contaminant supply (not shown) have been added. The sizes and concentration of contaminants added to reservoir 15 will vary depending, among other things, on the test being run, the rate of fluid flow through test filter 6, the volume of fluid in each reservoir 15 and the rate of flow of fluid 16 into junction 20. A typical test requires injecting 3 to 10mg/l of suitable contaminants into the upstream flow of test filter 6, with the rate of contaminant injection controlled by controller 102 on a real time basis in response to variables monitored and/or controlled by controller 102 (e.g., the system flow rate). These considerations will be discussed in greater detail below in the section on operation of test system 100.

Preferably at least two reservoirs 15 are used. With two reservoirs 15, first reservoir 15-1 can supply junction 20 with fluid 16 that contains a precise, known concentration of contaminants while second reservoir 15-2 is preparing a second batch of such fluid 16. In this manner, each of the multiple reservoirs 15 can be relatively small in volume compared to the requisite volume of a single reservoir 15. Smaller reservoirs 15 have the additional advantage of being easier to mix contaminants in fluid 16.

Referring now to FIGS. 17, 19, 20, 25 and 26, preferably reservoirs 15 are constructed the essentially the same as reservoir 180 of dilution subsystem 42, except that top plate 420 of reservoirs 15 (shown in FIG. 25; analogous to top plate 242 of reservoir 180 shown in FIG. 17) has additional hole 422 into which a precise charge of contaminants can be added manually or automatically under control of controller 102 using an appropriate injection system (not shown). Also, the top plate 242 of reservoirs 15 do not include a vent 248. For convenience, the structural parts of reservoirs 15 and the structural parts of the components attached to reservoirs 15 will be designated by the same names and numbers as the analogous parts of dilution subsystem 42; such parts connected to or controlled by controller 102 (e.g., a load cell) will be given different numeric designations.

For example, dilution subsystem includes load cell 262 (FIG. 17) while each reservoir 15 of contaminant injection subsystem 14 is weighed by load cell 426 (FIG. 26), which is part of scale 424. Scale 424 includes load cell 426 that generates a signal representative of the mass of its associated reservoir 15, fluid 44 in reservoir 15, and components attached to reservoir 15. This signal is conveyed to interface 428 via suitable cable 430. Interface 428 converts this signal to a form suitable for transmitting to controller 102 via cable 432.

Referring now to FIGS. 1, 2 and 23, in operation reservoir selection valve 406 channels fluid via pipes 409 from one reservoir 15 to pump 402 and from the other tank to pump 404. From pump 402 fluid flows via pipe 436 to junction 438. At junction 438 a portion of the fluid is diverted through pipe 442 to fill valve 408, which under control of controller 102 steers this fluid to the particular reservoir 15 from which it came, thereby recirculating the fluid to help maintain a uniform concentration of contaminants.

The remainder of the fluid from junction 438 flows to injection pump 412, first passing through shut off valve 410. Valve 410 is normally closed, but can be opened by controller 102 when controller 102 determines that contaminated fluid is needed for a test. From pump 412 fluid flows via pipe 444 through flow meter 1 to manual valve 414. Flow meter 1 is constructed substantially the same as flow meter 49 in FIG. 12 and functions in substantially the same manner. Valve 414 has three positions, the first position diverts the fluid to drain 416 and the second position stops flow through valve 414. The third position allows the fluid to flow through to pipe 18 and on to either the inlet of test pump 26 (at junction 20 as shown in FIG. 1) or the outlet of test pump 26 (at junction 21 as shown in FIG. 10).

From pump 404 fluid flows through pipe 446 to junction 418. Also connecting to junction 418 is pipe 73, which carries fluid from clean up subsystem 73 to refill reservoirs 15 under control of controller 102. However, for proper operation, controller 102 closes valve 74 to block the flow of fluid to junction 418 from cleanup subsystem 70 (or suitably controls this flow via variable restriction 76). From junction 418 fluid from pump 404 flows via pipe 434 to fill valve 408. Under control of controller 102, valve 408 passes this fluid into the particular reservoir 15 from which it came, thereby recirculating the fluid in this reservoir 15 to maintain a uniform distribution of contaminants in it.

Another function of fill valve 408 is to allow one reservoir 15 to be refilled with fluid from clean up subsystem 73 while the other reservoir 15 is idle or injecting fluid into junction 20. Controller 102 then orders clean up subsystem 70 to supply fluid to valve 408 via pipe 73, junction 418 and pipe 434. Controller 102 directs valve 408 to route this fluid to the particular reservoir 15 needing a refill.

Valves 408, 406 and 410 can be any suitable valve capable of control by controller 102. Suitable valve types include electrically controlled solenoid valves or pneumatic valves.

Manual valve 414 can direct fluid to drain 416. This can be done to purge contaminant injection subsystem 14 of fluid, or to sample the fluid contained in a particular reservoir 15.

Pump 412 plays an important role in the injection of contaminated fluid at either the outlet or the inlet of pump 26, depending on the particular embodiment of the present invention. Pump 412 is superior to alternative devices, such as a valve (not shown), because a valve is more vulnerable to clogging by contaminants. Preferably pump 412 is a positive displacement metering pump. Such a pump is superior to alternative pumps, such as a centrifugal pump, because a centrifugal pump is not capable of regulating flow or producing the pressures required.

Referring now to FIGS. 1, 2, 23 and 40, in FIG. 40 there is shown a flow chart depicting control loop 340 used by controller 102 to maintain the desired fluid flow rate from contaminant subsystem 14. In step 342 the contaminant flow rate is set. The rate can be chosen manually by an operator (not shown) at computer 161 (FIG. 14) or under control of software as a parameter in a test being run automatically by test system 100. In step 344 controller 102 monitors flow meter 1 to determine the present flow rate. Next in step 346 controller 102 determines whether the flow rate is within an acceptable range of the desired rate. If so, controller 102 loops back to step 344. If not, in step 348 controller 102 controls motor 413 to alter, as required, the flow rate imparted to the fluid by the series combination of pumps 402 and 412, respectively.

Cooling Subsystem

Referring now to FIGS. 1, 2, 27 and 28, cooling subsystem 80 is connected to and controlled by controller 102. Cooling subsystem 80 includes heat exchanger 310, input temperature monitor 312 (see FIG. 1) and output temperature monitor 314. The preferred configuration for heat exchanger 310 is of the type having a tube within a tube (not shown), with the tube in which the test fluid flows designed to have a constant uniform cross section. Heat exchanger 310 should not be of the type having header tanks and large flow area cooling tubes (with resulting reduced velocity), as these constructions affect the uniform suspension of contaminants in the fluid. The pipe (not shown) carrying fluid within heat exchanger 310 should maintain the uniform cross sectional area found throughout the fluid circuit in test system 100.

Preferably heat exchanger 310 is water cooled, with water supplied by any suitable water source, such as a well or a city water main (not shown). The water source is connected to and from heat exchanger 310 via pipes or other suitable water channel 316. Water channel 316 includes valve 320, connected to and controlled by controller 102 for regulating the flow of water to heat exchanger 310. Preferably valve 320 is a shut off valve, solenoid controlled and positioned upstream of the water inlet of heat exchanger 310. Alternatively valve 320 could be a variable restriction valve.

An optional output temperature monitor 314, connected to controller 102, can be positioned in fluid path 81 to monitor the temperature of the fluid exiting heat exchanger 310. Monitor 314 should not be needed, since controller 102 can adequately control the temperature of the fluid based on the temperatures monitored by monitor 312 (positioned at the outlet of test fixture 8), monitor 124 (positioned in reservoir 10) and the known cooling performance characteristics of heat exchanger 310. If used, preferably monitor 312 is based on a thermocouple, a simple and inexpensive device. Alternatively monitor 312 can be based on any other suitable temperature measuring device, such as a thermistor or a temperature sensitive resistor (not shown).

Figure 27:
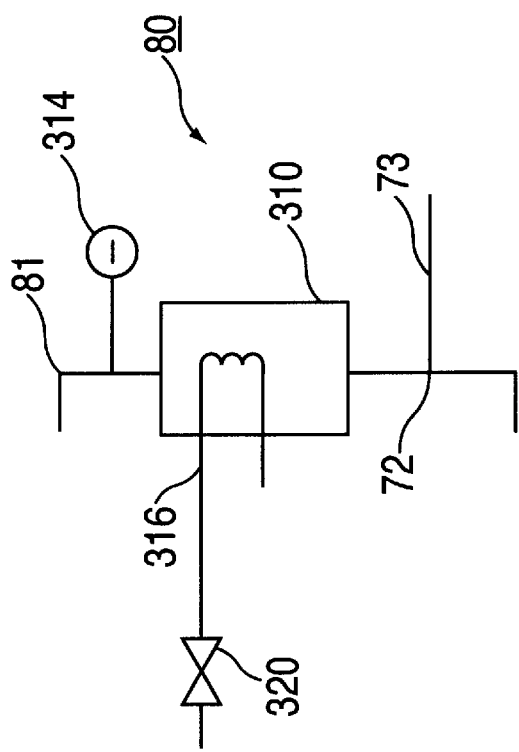
FIG. 27 is a block diagram of the cooling subsystem system of FIG. 1.

As shown in FIG. 27, valve 320 and temperature monitors 312 and 314 are connected to controller 102 via interface 322. Interface 320 includes any additional components (not shown) needed to connect valve 320 to controller 102 and to convert the signal from monitors 312 and 314 to signals suitable for sending to controller 102 over cable 324.

Controller Subsystem

Figure 14:
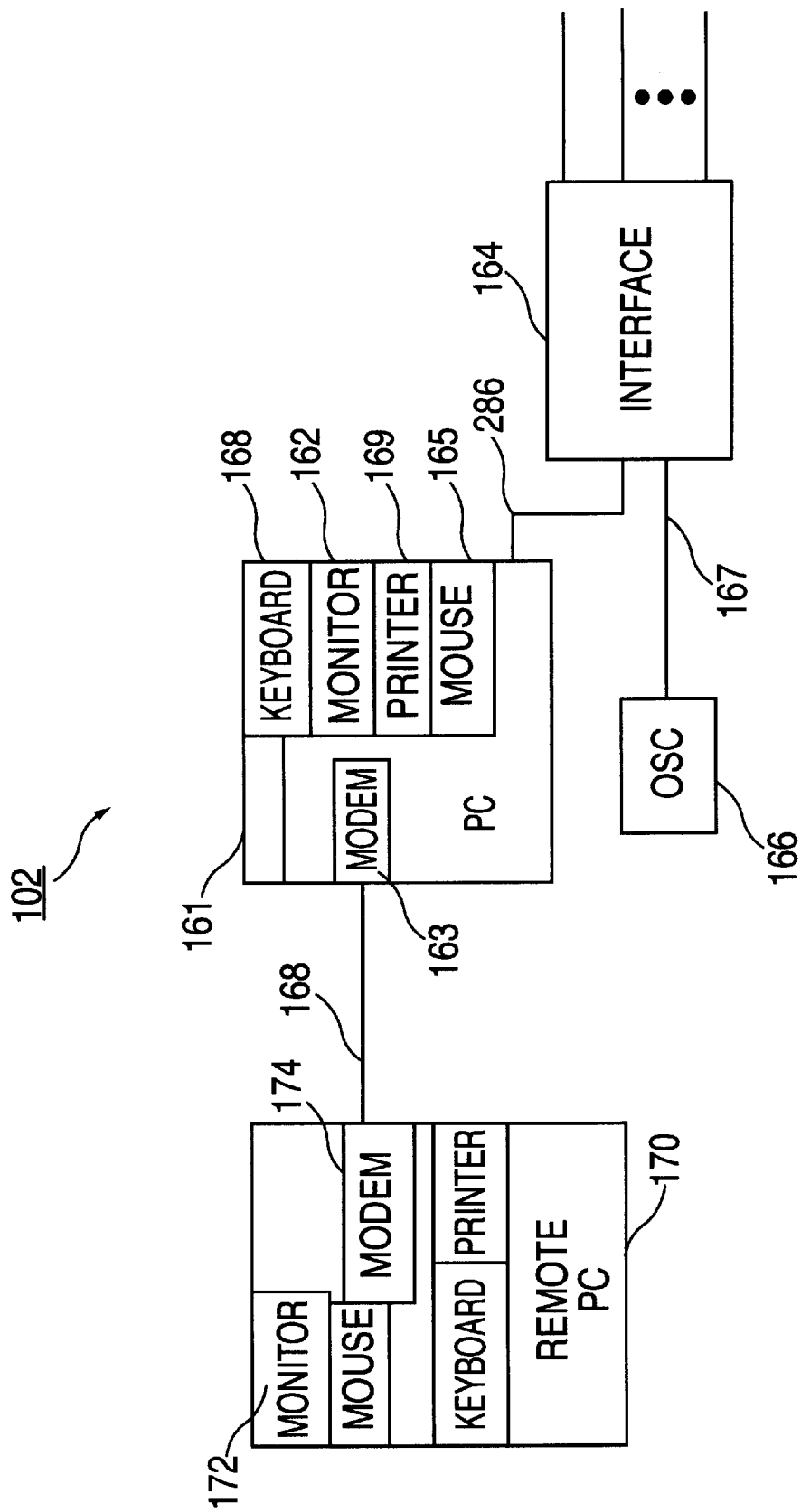
FIG. 14 is a block diagram of the controller of FIG. 2, including the remote monitor.
Figure 15:
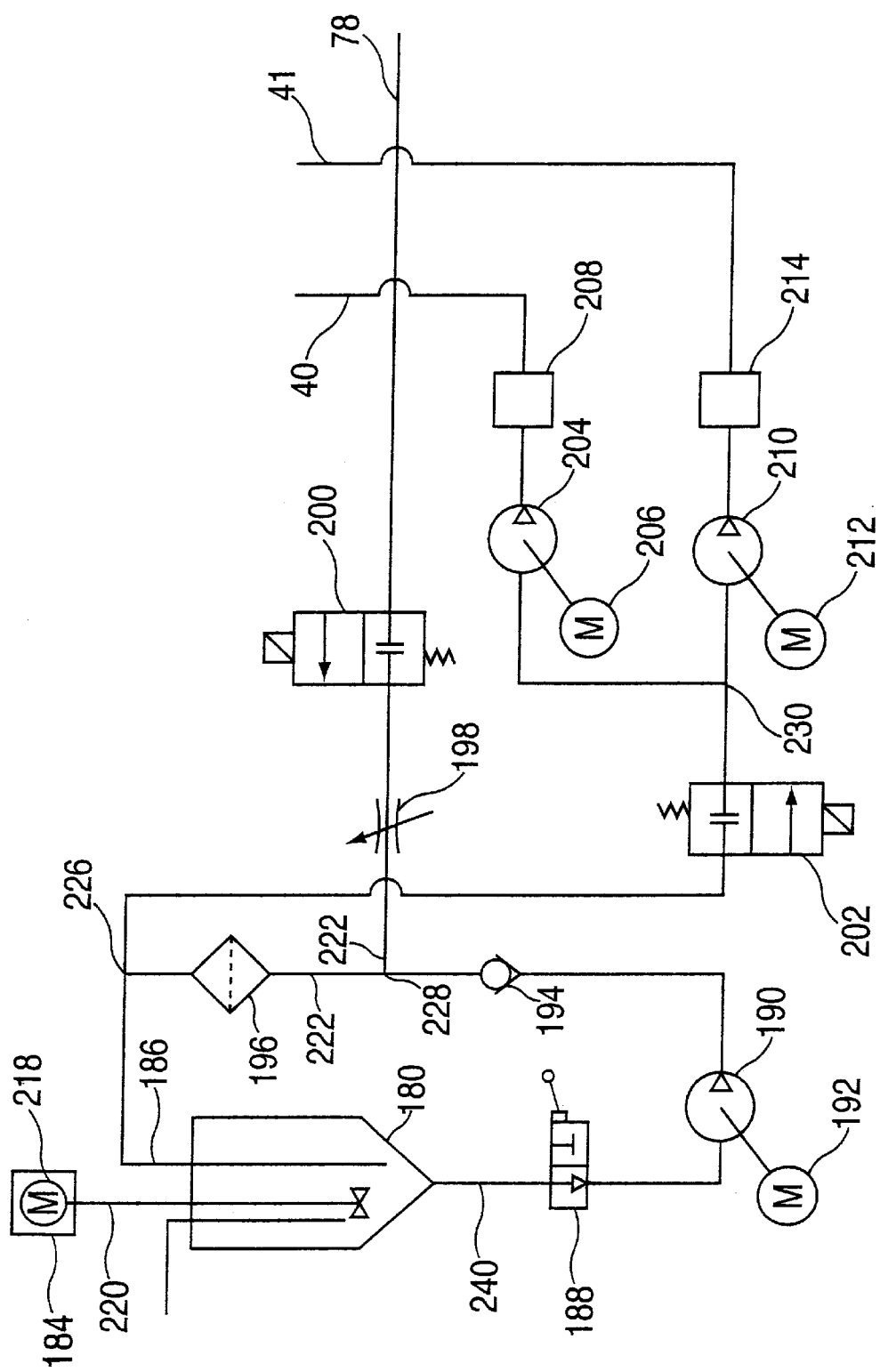
FIG. 15 is a schematic diagram of the dilution subsystem of FIG. 1.

Referring now to FIGS. 2 and 14, in FIG. 14 there is shown a block diagram of the components of controller 102. Controller 102 includes computer system 161, remote controller 170, interface 164, and display 166. Interface 164 gathers the signals received from the various components and subsystems of test system 100 and links these signals to suitable input and output ports (not shown) of computer system 161.

Interface 164 also connects certain of these signals to display 166 via connection 167. Display 166 is a monitor, such as an oscilloscope, suitable for displaying signals in real time. In particular, monitor 166 can display the signal from vibration monitor 52 indicating the vibrations of test fixture 8 (see FIGS. 1, 2 and 11). In addition (or in place of), display 166 can display the particle counts from contamination monitors 46 and 50 along the same time line but juxtaposed one above the other. In this manner, an observer (not shown) can judge qualitatively the performance of filter 6 in real time. With the signal from vibration monitor 52 displayed, the observer can judge such performance qualitatively as a function of the vibration of test fixture 8.

Preferably computer system 161 is a Windows (TM) based Pentium (TM) class personal computer or the equivalent. Computer 161 includes monitor 162, keyboard 168, printer 169, mouse 165 and remote communication device 163. Monitor 162, mouse 165 and keyboard 168 allow the test operator (not shown) to select and program the type of filter test, and the values of various parameters for the test. Once programmed, the operator can initiate and monitor the filter test.

Preferably remote controller 170 is also such a "Wintel" personal computer or the equivalent. Computer 170 includes display monitor 172 and remote communication device 174 compatible with device 163 and connected to device 163 via communication channel 168. Suitable devices 163 and 174 include point to point communication via telephone modems, cable modems, or wireless links (e.g., cellular phone or satellite telephony), or indirect link via any of these devices and an Internet connection. Preferably computer 172 and computer 161 have installed Symantec "PC Anywhere" (TM), a software program that allows remote monitoring and/or operation of one personal computer by a second personal computer. In this manner, a remote operator (not shown) can monitor and/or operate filter tests. Computer 161 includes printer 169 that can be used for printing the results of filter tests and for printing the status of the components and subsystems of test system 100.

Operation of Test System

Figures 29, 30:
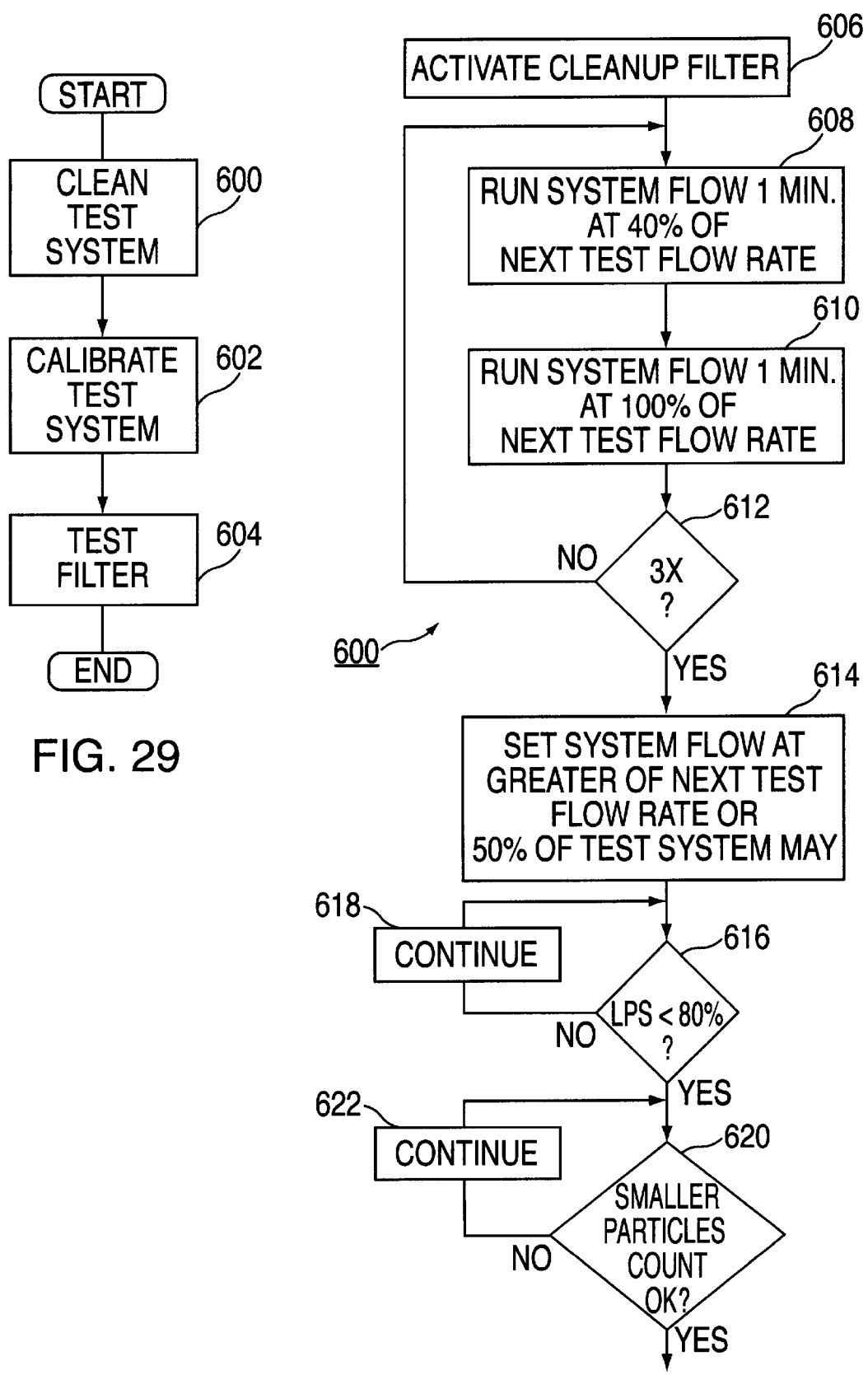
FIG. 29 is a flow chart of the basic test procedure implemented by the controller for the test system of FIG. 1.
FIG. 30 is a detailed flowchart of the clean test system step of the flowchart of FIG. 29.

Referring now to FIGS. 1, 2, 14 and 29, in FIG. 29 there is shown a simplified flow chart of the operation of test system 100 under control of controller 102. In step 600 test system 100 is cleaned with filter 6 absent from test fixture 8, in step 602 test system 100 is calibrated to account for the pressure drop through test fixture 8 without filter 6 present, and in step 604 filter 6 is placed in fixture 8 and tested.

Referring now to FIGS. 1, 2 14, 21, 29 and 30, in FIG. 30 there is shown a flowchart detailing the steps for step 600 of cleaning test system 100. First cleanup filter 292 is activate so the fluid passing through test system 100 is filtered of contaminants. Filter 292 is chosen to remove and maintain a test fluid cleanliness level of AS 4059 Class 1 (or better ). Next in step 608 test pump 26 is driven to maintain for one minute a flow rate through test fixture 8 ("system flow rate") of a predetermined fraction (e.g., 40%) of the rate specified for the next test to be conducted. Next in step 610 pump 26 maintains for one minute a system flow rate of 100% of the next test flow rate. In step 612 the series of steps 610 is repeated until each step 608 and 610 has occurred three times. Next in step 614 the system flow rate is set at the greater of the next test flow rate or 50% of the maximum permissible flow rate of test system 100.

In step 616 the contaminant level of the fluid is monitored by contaminant monitor 46 (or alternately by monitor 50 which should read substantially the same, given the current absence of test filter 6 from fixture 8). Controller 102 continues operating test system 100, directing the flow of fluid through cleanup filter 292 and monitoring particle counts. Step 616 is passed once this particle count holds below 80% of the largest particle passed rating through three consecutive count cycles of 30 seconds (with a dwell period of 30 seconds between counts). The data collection period and dwell period are not limited to 30 seconds, but can be any value desired by the operator of test system 100. The purpose of gathering data on particle counts in cycles of collection/dwell is to collect a sufficient amount of data to analyze the test performance of filter 6 without collecting extra data that may tax the real time analysis capability of test system 100 or the system's data storage capacity.

Thereafter, in step 620 controller 102 monitors the particle count in monitor 46 and/or monitor 50 for all particles smaller than the largest size particle of step 616. Step 620 is passed when the particle count for all such smaller particles counted falls below the normal distribution curve for the particular contaminant that will be injected by contaminant system 14 in the next test. The combined effect of steps 616 and 620 is to insure that the fluid in test system 100 has been filtered of all but an insignificant quantity and size of solid contaminants.

Figure 31:
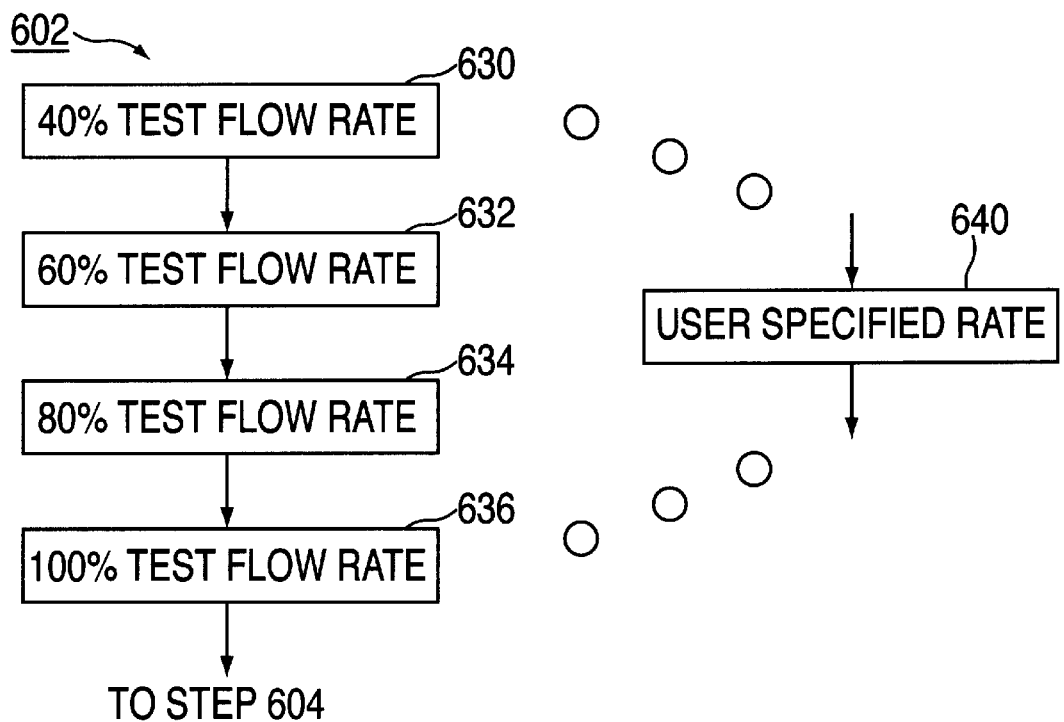
FIG. 31 is a detailed flowchart of the calibrate test system step of the flowchart of FIG. 29.

Referring now to FIGS. 1, 2, 14, 29 and 31, in FIG. 31 there is shown a flowchart of the steps implementing the calibrate test system step 602 of FIG. 29. This procedure calibrates test system 100 for the pressure drop through test fixture 8 without filter 6 present. First in steps 630, 632, 634 and 636 the system flow rate is set at 40%, 60%, 80% and 100%, respectively, of the maximum flow rate of the next test. The flow rates in the calibration of step 602 are run from slower to faster to speed up the process. FIG. 31 shows an optional user defined percentage rate step 640 that can be inserted into its proper place in the order. Each rate is run for a sufficient time for the flow to reach steady state, for test fluid temperature to stabilize to the desired value and for test fixture pressure monitor subsystem 56 (shown in FIG. 1) to obtain an accurate measurement of the pressure drop across fixture 8.

Figure 32:
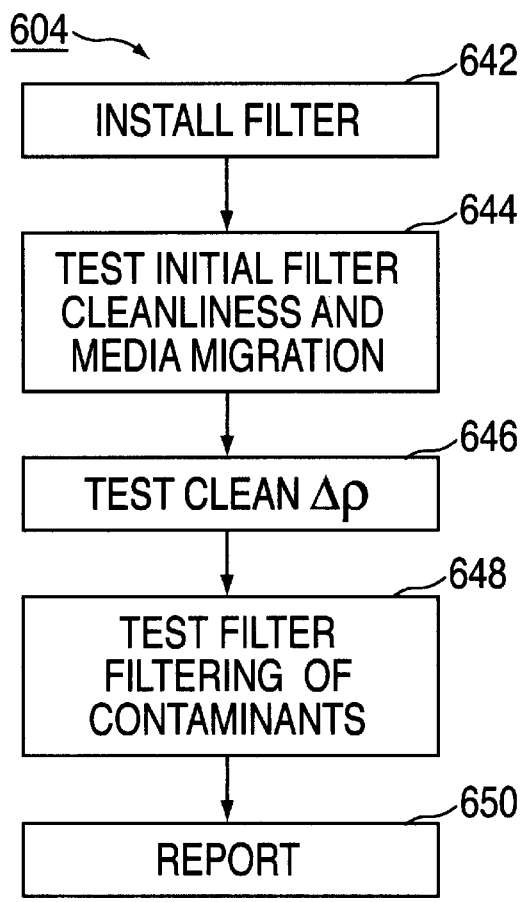
FIG. 32 is a flowchart of the test filter step of the flowchart of FIG. 29.

Referring now to FIG. 32 there is shown a simplified flowchart of the steps implementing test filter step 604 for FIG. 29. First in step 642 filter 6 is installed in fixture 8. Next in step 644 test system 100 tests the initial cleanliness of filter 6 and its media migration (as shown by particle count). Then in step 646 the pressure drop across test fixture 8 is determined for the now-clean filter 6 for the range of system flow rates and other conditions tested in the test system calibration of step 602. Then in step 648 filter 6 is subject to contaminants from contaminant injection subsystem 14 (see FIG. 1). Finally, in step 650 controller 102 generates a report of the test results. For further tests of additional filters 6, the steps 600, 602 and 604 of FIG. 29 are repeated.

Figures 33, 34:
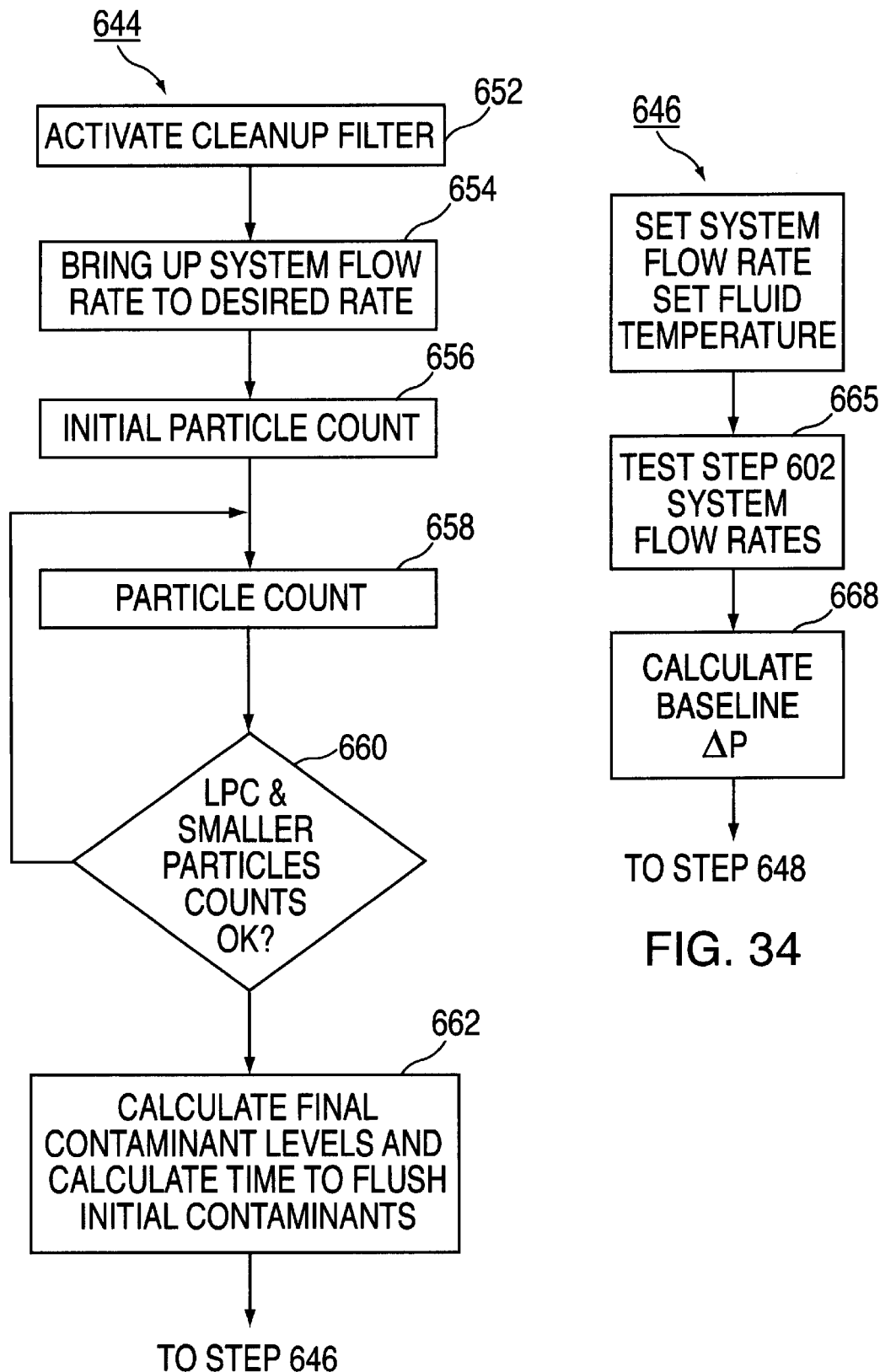
FIG. 33 is a detailed flowchart of the test initial filter cleanliness and media migration step of the flowchart of FIG. 32.
FIG. 34 is a detailed flowchart of the test clean differential pressure step of the flowchart of FIG. 32.

Referring now to FIG. 33, there is shown a detailed flowchart of step 644 of FIG. 32 in which controller 102 tests the initial cleanliness of filter 6, including any migration of filtering media (not shown) from filter 6. In step 652 cleanup filter 292 remains active. In step 654 with filter 6 previously installed (in step 642), the system flow rate is brought up to the desired rate. Then in step 656 the initial particle count is made by respective upstream and downstream monitors 46 and 50. To insure accurate counting of initial contaminants and media migration, this count should begin within 30 seconds of the initial fluid flow through filter 6. As in other steps involving particle counting, the operator can configure test system 100 to gather data on particle counts either continuously or in cycles of data collection/dwell. Experience has shown it is sufficient in many tests in this step to count for 30 seconds then dwell (no counting) for an additional 30 seconds.

In step 658 monitors 46 and 50 count particles on a operator-selectable duty cycle, such as a 50% duty cycle: a thirty second count followed by a 30 second dwell time in which no record is kept of the particle count. In step 660 controller 102 compares the particles counted for the largest particle passed size for filter 6 and the particles smaller than this for the counts in respective steps 616 and 620 in FIG. 30 (clean fluid). Filtering of fluid through both filter 6 and cleanup filter 292 continues until these counts fall to within 10% of the values obtained for steps 616 and 620.

Next in step 662 controller 102 calculates the particles per milliliter for each measurement period for monitors 46 and 50 for each relevant particle size. Controller 102 also calculates the time interval required to flush particulate contaminants from filter 6 to the levels required in step 660. This is a measure of the initial level of contaminants and/or media migration of filter 6.

Referring now to FIG. 34, there are shown the steps of the test clean filter differential pressure step 646 of FIG. 32. First in step 664 the system flow rate and fluid temperature are set to rated values. Next in step 665 the pressure drop across filter 6 in test fixture 8 is monitored by pressure monitoring subsystem 56 for all of the flow rates tested with empty test fixture 8 in step 602. Finally in step 668 a set of baseline (clean) filter 6 pressure drops are determined for each system flow rate tested by subtracting the pressure drop values for test fixture 8 only (determined in step 602) from those determined in step 665.

Figure 35:
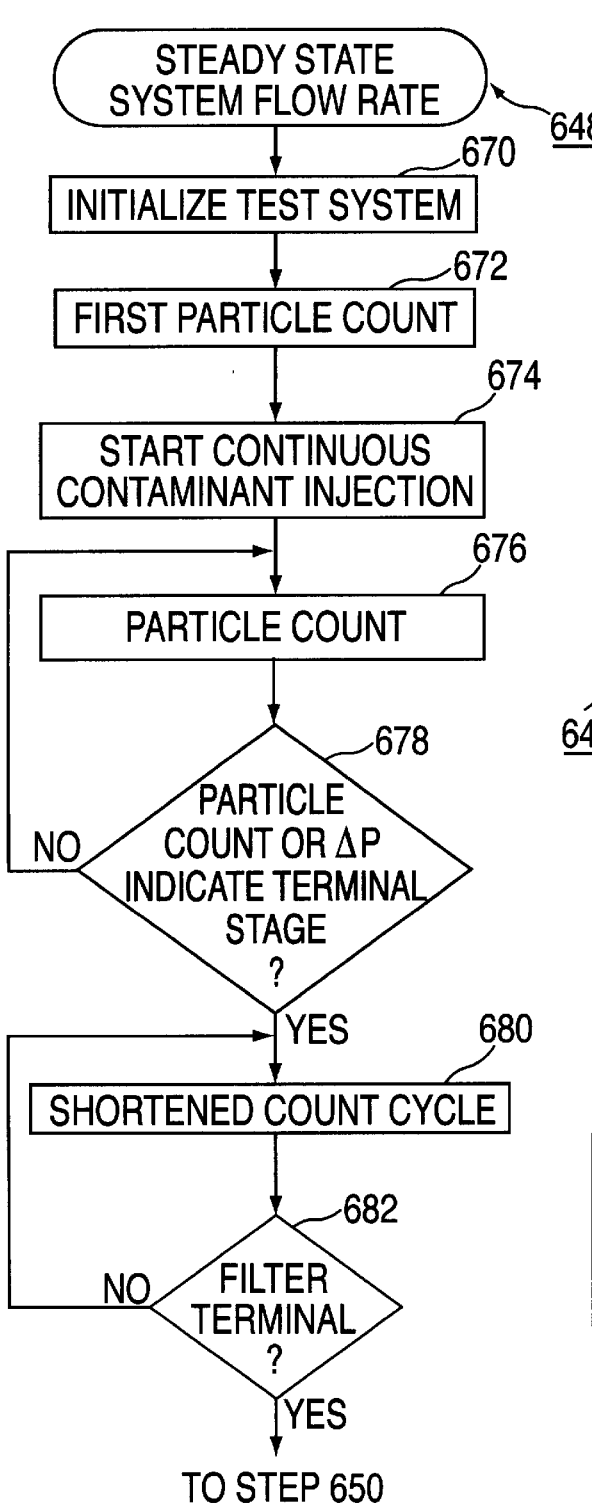
FIG. 35 is a detailed flowchart of the test filter filtering of contaminants step of the flowchart of FIG. 32 for a steady state test system flow rate.

Referring now to FIG. 35, there is shown a detailed flowchart of the filter contaminant testing step 648 of FIG. 32 for a filter 6 undergoing a steady system flow rate. In step 670 test system 100 is initialized according to the dictates of the particular test. In particular, for single pass tests controller 102 leaves in line clean up filter 292 and for multi-pass tests controller 102 switches out filter 292. Furthermore, controller 102 sets fluid temperature to rated levels, employing heater 66 of reservoir 10 or cooling subsystem 80 as necessary. Pump 26 drives the fluid to the desired system flow rate.

In step 672 controller 102 orders monitors 46 and 50 to begin their first particle count, with the count/dwell cycle pre-selected by the operator. A typical count/dwell cycle is a 30 second counting period and a 150 second dwell time before the next counting period. Next in step 674 at the end of the first counting period, controller 102 instructs contaminant injection subsystem 14 to begin injecting contaminated fluid 15. Fluid 15 is injected either at the inlet or the outlet of pump 26, depending upon the particular configuration of test system 100.

In step 676 respective upstream and downstream contaminant monitors 46 and 50 count particles in an operator selected cycle of counting and dwell, such as a cycle of 30 seconds of counting followed by 150seconds of dwell. Controller 102 records this data together with all other test parameters specified for the particular test and adjusts the various systems as necessary to maintain a continuous injection of contaminants, system flow rate, fluid temperature, among other system parameters specified. The rate of contaminants injected in step 674 will depend on the requirements of the particular test being run. A typical value is such as to produce an upstream gravimetric level of 5 mg of contaminants per liter of fluid. Dilution subsystem 42 is employed by controller 102 as necessary to maintain contaminant monitors 46 and 50 within their range.

Step 678 monitors the differential pressure measured by pressure monitor subsystem 56. A shortened particle counting cycle is initiated in step 680 when the differential pressure monitored deviates by a predetermined amount from the differential pressure determined in clean filter differential pressure step 646. A typical trigger amount is a differential pressure of 5 pounds per square inch. This amount is selected to indicate that filter 6 may be approaching the accelerated increase towards the terminal pressure differential specified by the test specifications of filter 6. The count and dwell periods of the shortened counting cycle are specified by the operator in advance of the test.

The shortened count continues until in step 682 it is determined that filter 6 has reached the terminal pressure differential specified by the test specifications of filter 6. Alternatively, the test may be continued until one or more of the following conditions is detected by controller 102:

the differential pressure across filter 6 ceases to increase with the continuous addition of contaminants;

there occurs a sudden decrease in differential pressure; or there occurs a significant decrease of filtration efficiency.

At this point controller 102 terminates the test and enters the reporting stage of step 650.

Figure 36:
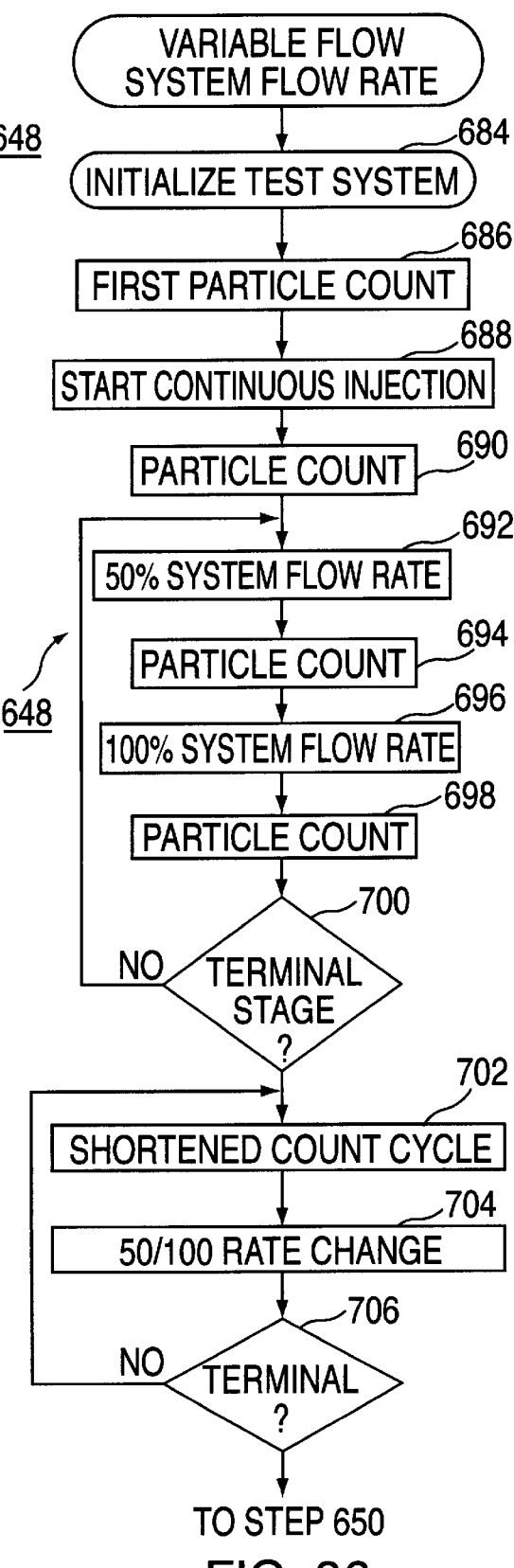
FIG. 36 is a detailed flowchart of the test filter filtering of contaminants step of the flowchart of FIG. 32 for a variable rate test system flow rate.

Referring now to FIG. 36, there is shown a detailed flowchart of the filter contaminant testing step 648 of FIG. 32 for a filter 6 undergoing a variable system flow rate. In step 684 test system 100 is initialized according to the dictates of the particular test. In particular, for single pass tests controller 102 leaves in line clean up filter 292 and for multi-pass test controller 102 switches out filter 292. Furthermore, controller 102 brings fluid temperature up to rated levels, employing heater 66 of reservoir 10 as necessary. Controller 102 controls pump 26 to pump the fluid to the desired system flow rate pre-selected by the operator.

In step 686 controller 102 orders monitors 46 and 50 to begin their first particle count, with the count/dwell cycle pre-selected by the operator. A typical count/dwell cycle is a 30 second counting period and a 150 second dwell time before the next counting period. Next in step 688 at the end of the first counting period, controller 102 instructs contaminant injection subsystem 14 to begin injecting contaminated fluid 15. The rate of contaminants injected in step 688 will depend on the requirements of the particular test being run. A typical value is such as to produce an upstream gravimetric level of 5 mg of contaminants per liter of fluid. Fluid 15 is injected either at the inlet or the outlet of pump 26, depending upon the particular configuration of test system 100.

In step 690 respective upstream and downstream contaminant monitors 46 and 50 count particles in a cycle of counting and dwell preselected by the operator prior to the test being conducted. A typical count/dwell cycle is 30 seconds of counting followed by 150 seconds of dwell. Controller 102 records the data from monitors 46 and 50 and adjusts the various subsystems as necessary to maintain a steady injection of contaminants, steady system flow rate, set fluid temperature, among other system parameters specified and controlled for the test. Dilution subsystem 42 is employed by controller 102 as necessary to maintain the level of contaminants in the fluid passing through contaminant monitors 46 and 50 within their measurable range. Controller 102 adjusts the contamination measurements received from monitors 46 and 50 to reflect the amount of fluid 44, if any, controller 102 orders injected by dilution subsystem 42 into monitors 46 or 50.

Up to this point the variable flow implementation, shown in FIG. 36, of filter testing step 684 of FIG. 32 has been essentially the same as the steady state implementation shown in FIG. 35. Now in the variable flow implementation the system flow rate is cycled or alternated between the flow rate set in step 684 and some fraction of this rate until controller 102 deduces that filter 6 is terminal. In particular, in step 692 controller 102 controls the subsystems of test system 100 to reduce the system flow rate to a predetermined fraction of the initial rate of step 684. Typically this fraction is 50%. However, the operator can select any other suitable fraction. Controller 102 automatically adjusts the various subsystems of test system 100 (e.g., contaminant injection subsystem 14 and cooling subsystem 80) to operate properly at this reduced flow rate.

This reduced system flow rate is maintained by controller 102 for a predetermined period, during which in step 694 contaminant monitors 46 and 50 count contaminant particles in a count/dwell cycle pre-selected by the operator prior to the start of the test. A typical count/dwell cycle is a 30 second count followed by a 150 second dwell. A typical predetermined period for the reduced system flow rate is three count/dwell cycles.

Next in step 696 controller 102 returns the system flow rate to the value initially set in step 684. This "100%" system flow rate is maintained by controller 102 for a predetermined period, during which in step 698 contaminant monitors 46 and 50 count contaminant particles in a count/dwell cycle pre-selected by the operator prior to the start of the test. A typical count/dwell cycle is a 30 second count followed by a 150 second dwell. A typical predetermined period for the returned system flow rate is three count/dwell cycles.

In step 700 controller 102 monitors the differential pressure measure by pressure monitor subsystem 56. A shortened particle counting cycle is initiated in step 702 when the differential pressure monitored deviates by a predetermined amount from the differential pressure determined in clean filter differential pressure step 646. A typical trigger amount is a differential pressure of 5 pounds per square inch. This predetermined amount is selected by the operator when configuring the test based on knowledge of the performance characteristics of the particular type of filter 6 being tested. The predetermined amount chosen indicates that filter 6 may be approaching the terminal pressure differential specified by the test specifications of filter 6.

The count and dwell periods of the shortened counting cycle of step 702 are specified by the operator in advance of the test. As with other count/dwell cycle choices, the operator bases the choice of count/dwell cycle on the known behavior of this type of filter 6 and balances the need for sufficient data to accurately evaluate the performance of filter 6 against the desire to minimize the data capture and data evaluation tasks of controller 102.

In step 704 controller 102 cycles the system flow rate between the reduced value of step 692 (e.g., 50% of initial system flow rate) and the 100% of the system flow rate of step 696 specified by the operator for the test. Preferably the reduced flow rate and the 100% flow rate are maintained for the same time periods set in respective steps 692 and 694.

The shortened count cycle initiated by step 702 continues until in step 706 controller 102 determines that filter 6 has reached the terminal pressure differential specified by the test specifications of filter 6. This is indicated by the differential pressure across the filter ceasing to increase with the continuous addition of contaminants, by a sudden decrease in differential pressure, or by a significant decrease of filtration efficiency. At this point controller 102 terminates the testing of filter 6 and enters the reporting stage of step 650.

Referring now to FIG. 37, there is shown a summary of the contents of a test report 708 for report step 650 of FIG. 32. The test report includes: a table of contents, a description of the test that was conducted, a listing of the test specifications (e.g., range of system flow rates), data collected in the course of the test showing flow rate versus pressure drop across the test filter; a graph of the flow pressure with respect to time; data on the cleanliness of the test system prior to placing the test filter 6 in test fixture 8; data collected in the course of the test showing the initial contamination level of the test filter; data collected in the course of the test showing the final contamination level of the test filter; data collected in the course of the test showing test-specific performance (e.g., dynamic efficiency filtration test data); a plot of data collected in the course of the test showing filtration efficiency versus the pressure differential measured across test filter 6; a plot of data showing contaminant capacity of filter 6 versus the life of test filter 6 in the test; a numerical summary, including time average total performance data; an interpretation of the results of the filter test; and references.

Other Applications

Figure 42:
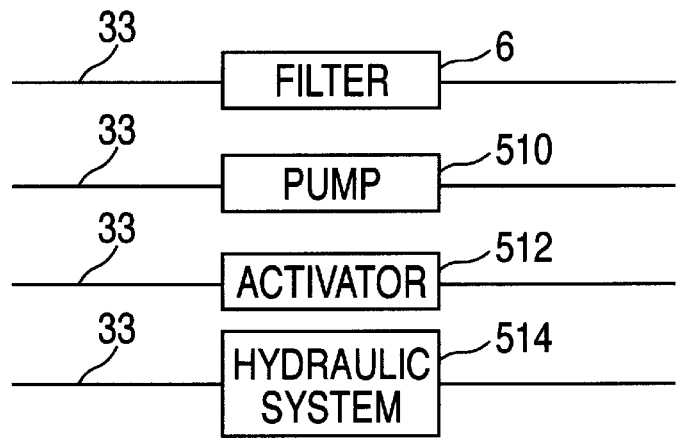
FIG. 42 is a block diagram of the various hydraulic components and systems that can be tested by the test system of FIG. 1.

Referring now to FIGS. 1 and 42, test system 100 can be used to test hydraulic elements other then filters 6. In particular, instead of filter 6, any other hydraulic element can be tested, including a hydraulic powered pump 510, hydraulic actuator 512, or even a hydraulic system 514 of an aircraft, a boat or other vehicle. In the case of a hydraulic system 514 that is part of a relatively large vehicle (not shown), test system 100 could be mounted on a suitable vehicle, such as a trailer (not shown) so that test system 100 could be moved to the site of the vehicle.

It is to be understood that even though various embodiments and advantages of the present invention have been set forth in the foregoing description, the above disclosure is illustrative only, and changes may be made in detail, yet remain within the broad principles of the invention. Therefore, the present invention is limited only by the appended claims.

What is claim is:

1. An apparatus for testing hydraulic components, comprising:
    a. a test fixture for housing a hydraulic component to be tested, the test fixture including inlet and outlet connections;
    b. a first fluid reservoir containing fluid substantially free of contaminants before a test is commenced and including inlet and outlet connections;
    first fluid channel that connects the outlet of the fluid reservoir to the inlet of he test fixture;
    c. a test pump positioned in and connected to the first fluid channel for pumping fluid to the inlet of the test fixture;
    d. a first junction positioned in the first fluid channel;
    e. a second junction positioned in the first fluid channel between the inlet of the test fixture and the first junction;
    first contaminant monitoring system having inlet and outlet connections, with the inlet connected to the second junction for receiving fluid the second junction diverts from the inlet of the test fixture, for monitoring the contaminants in the fixture inlet fluid;
    f. a second fluid channel that connects the outlet of the test fixture to the inlet of the first reservoir;
    g. a third junction positioned in the second fluid channel;
    h. a second contaminant monitoring system having inlet and outlet connections, with the inlet connected to the third junction for receiving fluid the third junction diverts from the outlet of the test fixture, for monitoring the contaminants in the fixture outlet fluid;
    i. a pressure monitor connected to the second and third junctions for measuring the pressure drop across the inlet and outlet of the test fixture;
    j. a contaminant injection system for injecting a predetermined charge of contaminants into the inlet of the test fixture, the contaminant system including:
        a plurality of second fluid reservoirs, each capable of containing a slurry consisting of a known volume of fluid mixed with a charge of contaminants of known mass, each second reservoir including an inlet for receiving fluid, an inlet for receiving a charge of contaminants and an outlet for discharging the contaminant slurry;
        a first valve connected to the outlets of each second reservoir and to the first junction for connected the outlet of one second reservoir to the first junction;
        a third fluid channel that connects the outlet of the first fluid reservoir to each of the second fluid reservoirs for filling the second fluid reservoirs with substantially clean fluid from the first fluid reservoir; and
        a second valve positioned in can connected to the third fluid channel and the fluid inlets of each of the second reservoirs for switchably connecting the outlet of the first reservoir to selected fluid inlets of the second reservoirs;
    whereby the first valve can be positioned to allow one second reservoir to discharge a contaminant slurry into the first junction while the second valve is positioned to allow at least one other second reservoir to receive fluid from the first reservoir via the third fluid channel.

2. The apparatus of claim 1, further including:
a heater operably connected to the first reservoir for heating fluid in the first reservoir;
a first temperature monitor positioned in proximity to the first reservoir for measuring the temperature of the fluid in the first reservoir;
a second temperature monitor positioned in proximity to the test fixture in the flow of fluid to or from the test fixture for measuring the temperature of the fluid flowing through the test fixture and the hydraulic component; and
a controller operably connected to the first and second temperature monitors and to the heater for controlling the heater in response to the temperatures sensed by the first and second temperature monitors.

3. The apparatus of claim 2, wherein the controller controls the heater to maintain the temperature monitored by the second temperature monitor at substantially a predetermined temperature.

* * * * *